US008447091B2

(12) United States Patent
Eda

(10) Patent No.: US 8,447,091 B2
(45) Date of Patent: May 21, 2013

(54) ULTRASONIC OBSERVATION APPARATUS, OPERATION METHOD OF THE SAME, AND COMPUTER READABLE RECORDING MEDIUM

(75) Inventor: Hirotaka Eda, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/491,782

(22) Filed: Jun. 8, 2012

(65) Prior Publication Data

US 2013/0011038 A1 Jan. 10, 2013

Related U.S. Application Data

(63) Continuation of application No. PCT/JP2011/076605, filed on Nov. 11, 2011.

(30) Foreign Application Priority Data

Nov. 11, 2010 (JP) ................................ 2010-253291

(51) Int. Cl.
*G06K 9/00* (2006.01)
*A61B 8/00* (2006.01)

(52) U.S. Cl.
USPC ............................ 382/131; 382/274; 600/437

(58) Field of Classification Search
USPC .................. 382/100, 103, 106–107, 128–134, 382/162, 168, 173, 181, 199, 214, 232, 254, 382/274, 276, 286–291, 305, 312; 600/439, 600/442, 454, 437
See application file for complete search history.

(56) References Cited

U.S. PATENT DOCUMENTS

| 6,454,713 B1* | 9/2002 | Ishibashi et al. ............... 600/439 |
| 6,875,176 B2* | 4/2005 | Mourad et al. ................. 600/442 |
| 2004/0019276 A1* | 1/2004 | Kim et al. ...................... 600/437 |
| 2004/0152983 A1* | 8/2004 | Vince et al. .................... 600/454 |
| 2005/0203405 A1 | 9/2005 | Tsujita |
| 2007/0160275 A1* | 7/2007 | Sathyanarayana ............. 382/128 |

FOREIGN PATENT DOCUMENTS

| JP | 2004-049925 A | 2/2004 |
| JP | 2005-253827 A | 9/2005 |
| JP | 2007-097671 A | 4/2007 |
| JP | 2007-524431 A | 8/2007 |

(Continued)

OTHER PUBLICATIONS

International Search Report PCT/JP2011/076605 dated Jan. 31, 2012.

*Primary Examiner* — Seyed Azarian
(74) *Attorney, Agent, or Firm* — Scully, Scott, Murphy & Presser, P.C.

(57) ABSTRACT

A data space in which a coordinate system is set having, as components, feature data extracted by approximation with respect to frequency spectrums of received ultrasonic waves, when a feature point of a frequency spectrum at a data position is present within a first area in an i-th frame (i is a positive integer) in a display and moves closer to a second area, having a lower priority than the first area, in subsequent (i+1)-th frame; an ultrasonic observation apparatus generates image data by setting a virtual feature point that is far off from the second area as compared to the latest feature point and that is within or around the first area, and by replacing visual information corresponding to the latest feature point in the (i+1)-th frame of the predetermined data position with visual information corresponding to the virtual feature point, and then displays the image data.

15 Claims, 22 Drawing Sheets

FOREIGN PATENT DOCUMENTS

| | | |
|---|---|---|
| JP | 2009-523059 A | 6/2009 |
| WO | WO 2004/069027 A2 | 8/2004 |
| WO | WO 2005/122906 A1 | 12/2005 |
| WO | WO 2007/082218 A2 | 7/2007 |

\* cited by examiner

ULTRASONIC OBSERVATION APPARATUS, OPERATION METHOD OF THE SAME, AND COMPUTER READABLE RECORDING MEDIUM

CROSS REFERENCES TO RELATED APPLICATIONS

This application is a continuation of PCT international application Ser. No. PCT/JP2011/076605 filed on Nov. 11, 2011 which designates the United States, incorporated herein by reference, and which claims the benefit of priority from Japanese Patent Applications No. 2010-253291, filed on Nov. 11, 2010, incorporated herein by reference.

BACKGROUND OF THE INVENTION

1. Field of the Invention

The present invention relates to an ultrasonic observation apparatus, an operation method of the ultrasonic observation apparatus, and a computer readable recording medium for enabling observation of tissues of a specimen using ultrasonic sound waves.

2. Description of the Related Art

Typically, in order to perform screening for breast cancer using ultrasonic sound waves, a technology called ultrasonic elastography is known (for example, see International Laid-open Pamphlet No. 2005/122906). The ultrasonic elastography is a technology which makes use of the fact that cancer tissues or tumor tissues inside a body have different hardness depending on the disease progression or depending on the body nature. In this technology, while continually applying external compression to the screening location, the strain amount or the degree of elasticity of the body tissues at the screening location is measured using ultrasonic sound waves, and the measurement result is displayed in the form of cross-sectional images.

SUMMARY OF THE INVENTION

An ultrasonic observation apparatus according to the present invention transmits ultrasonic sound waves to a specimen and receives ultrasonic sound waves reflected from the specimen, the ultrasonic observation apparatus comprising: a frequency analyzing unit that calculates frequency spectrums at a plurality of data positions which are set with respect to the ultrasonic sound waves that have been received; a feature data extracting unit that performs approximation with respect to the frequency spectrums calculated by the frequency analyzing unit and extracts a single set or a plurality of sets of feature data of the frequency spectrums; an image processing unit that sequentially generates feature-data image data containing information related to the feature data extracted by the feature data extracting unit; and a display unit that sequentially displays images corresponding to the feature-data image data generated sequentially by the image processing unit, wherein in a feature data space in which it is possible to set a coordinate system having at least some of the single set or the plurality of sets of feature data as coordinate components, when a feature point of a frequency spectrum at a particular data position is present within a predetermined first type area in an i-th frame (where i is a positive integer) in the display unit and moves closer to a second type area, which has a lower priority for image display than the first type area, in subsequent (i+1)-th frame, the image processing unit generates the feature-data image data by setting a virtual feature point at a position that is far off from the second type area as compared to the position of latest feature point and that is within or around the first type area, and by replacing visual information corresponding to the latest feature point in the (i+1)-th frame of the predetermined data position with visual information corresponding to the virtual feature point.

An operation method of an ultrasonic observation apparatus according to the present invention transmits ultrasonic sound waves to a specimen and receives ultrasonic sound waves reflected from the specimen, the operation method comprising: calculating, by a frequency analyzing unit, that includes analyzing frequencies of the received ultrasonic sound waves and calculating a frequency spectrum; extracting that includes performing approximation with respect to the frequency spectrum and extracting a single set or a plurality of sets of feature data of the frequency spectrum; generating, by an image processing unit, that includes generating feature-data image data containing information related to the feature data; and displaying, by a displaying unit, that includes displaying an image corresponding to the feature-data image data, wherein the calculating that includes calculating the frequency spectrum up to the displaying that includes displaying the image is performed in a repeated manner, and in a feature data space in which it is possible to set a coordinate system having at least some of the single set or the plurality of sets of feature data as coordinate components, when a feature point of a frequency spectrum at a particular data position is present within a predetermined first type area in an i-th frame (where i is a positive integer) in the display unit and moves closer to a second type area, which has a lower priority for image display than the first type area, in subsequent (i+1)-th frame, the feature-data image data is generated by setting a virtual feature point at a position that is far off from the second type area as compared to the position of latest feature point and that is within or around the first type area, and by replacing visual information corresponding to the latest feature point in the (i+1)-th frame of the predetermined data position with visual information corresponding to the virtual feature point.

A non-transitory computer readable recording medium according to the present invention has an executable program stored thereon, wherein the program instructs a processor to perform: calculating, by a frequency analyzing unit, that includes analyzing frequencies of the received ultrasonic sound waves and calculating a frequency spectrum; extracting that includes performing approximation with respect to the frequency spectrum and extracting a single set or a plurality of sets of feature data of the frequency spectrum; generating, by an image processing unit, that includes generating feature-data image data containing information related to the feature data; and displaying, by a displaying unit, that includes displaying an image corresponding to the feature-data image data, wherein the calculating that includes calculating the frequency spectrum up to the displaying that includes displaying the image is performed in a repeated manner, and in a feature data space in which it is possible to set a coordinate system having at least some of the single set or the plurality of sets of feature data as coordinate components, when a feature point of a frequency spectrum at a particular data position is present within a predetermined first type area in an i-th frame (where i is a positive integer) in the display unit and moves closer to a second type area, which has a lower priority for image display than the first type area, in subsequent (i+1)-th frame, the feature-data image data is generated by setting a virtual feature point at a position that is far off from the second type area as compared to the position of latest feature point and that is within or around the first type area, and by replacing visual information corresponding to the latest feature point in the (i+1)-th frame of the predetermined data position with visual information corresponding to the virtual feature point.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Exemplary illustrative embodiments of the present invention (hereinafter, referred to as "embodiments") are explained below in detail with reference to the accompanying drawings.

First Embodiment

Figure 1:
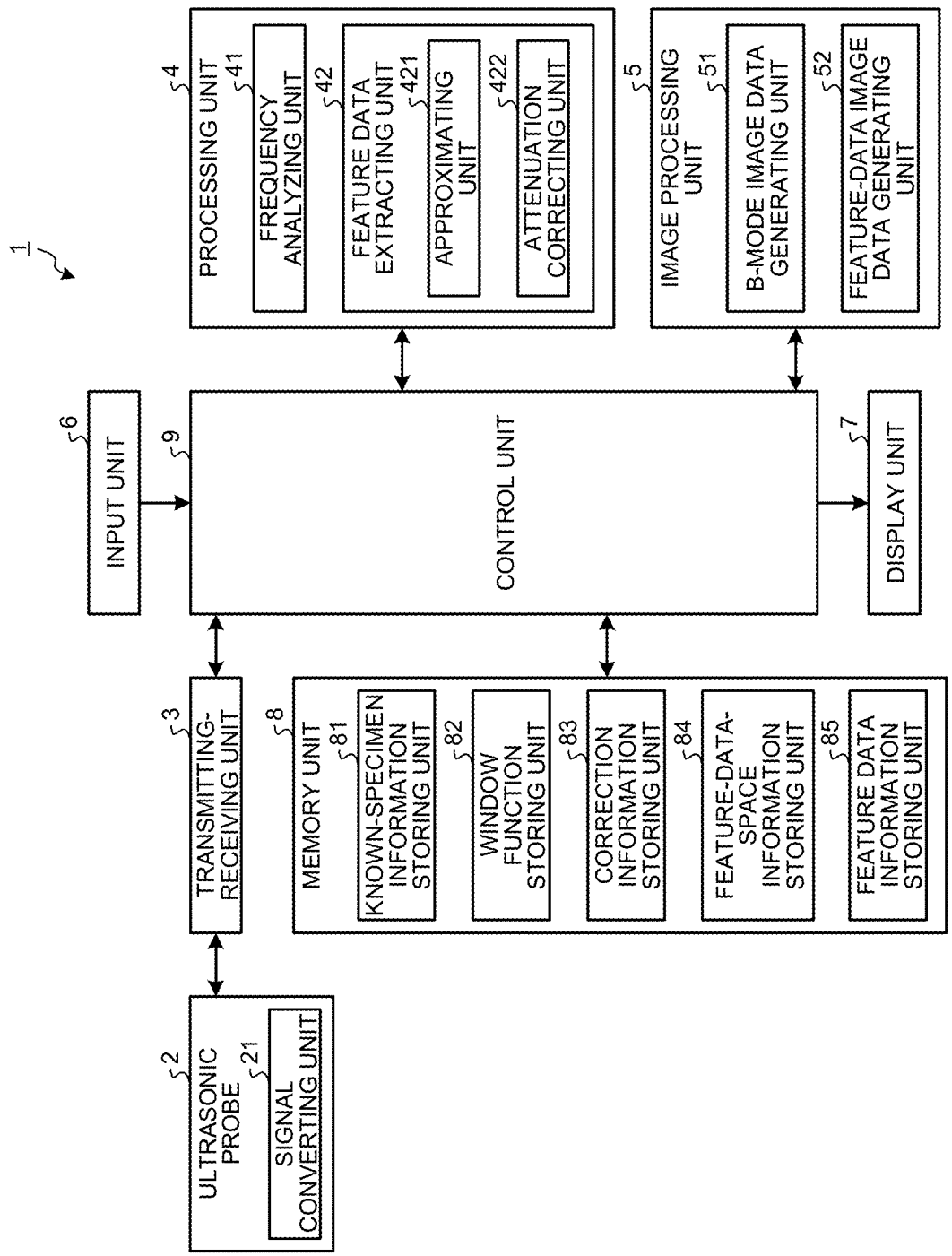
FIG. 1 is block diagram illustrating a configuration of an ultrasonic observation apparatus according to a first embodiment of the present invention.

FIG. 1 is block diagram illustrating a configuration of an ultrasonic observation apparatus according to a first embodiment of the present invention. An ultrasonic observation apparatus 1 illustrated in FIG. 1 is an apparatus for observing the tissue characterization of a target specimen for observation using ultrasonic sound waves.

The ultrasonic observation apparatus 1 includes an ultrasonic probe 2 that outputs an ultrasonic pulse to the outside and receives an ultrasonic echo obtained by reflection on the outside; a transmitting-receiving unit 3 that transmits electrical signals to and receives electrical signals from the ultrasonic probe 2; a processing unit 4 that performs predetermined processing on electrical echo signals which are obtained by means of conversion of the ultrasonic echo; an image processing unit 5 that generates a variety of image data using the electrical echo signals which are obtained by means of conversion of the ultrasonic echo; an input unit 6 that is configured with an interface such as a keyboard, a mouse, or a touch-sensitive panel, and that receives input of a variety of information; a display unit 7 that is configured with a liquid crystal display panel or an organic EL display panel, and that displays a variety of information including the images generated by the image processing unit 5; a memory unit 8 that is used to store a variety of information including information related to the tissue characterizations of known specimens; and a control unit 9 that controls the operations of the ultrasonic observation apparatus 1.

The ultrasonic probe 2 converts electrical pulse signals that are received from the transmitting-receiving unit 3 into ultrasonic pulse (acoustic pulse signals), and includes a signal converting unit 21 for converting the ultrasonic echo that is obtained by reflection from an outside specimen into electrical echo signals. Meanwhile, the ultrasonic probe 2 can be configured to have an ultrasonic transducer performing scanning in a mechanical manner or can be configured to have a plurality of ultrasonic transducers performing scanning in an electronic manner.

The transmitting-receiving unit 3 is electrically connected to the ultrasonic probe 2. With that, the transmitting-receiving unit 3 transmits pulse signals to the ultrasonic probe 2 and receives echo signals representing reception signals from the ultrasonic probe 2. More particularly, based on a predetermined waveform and a predetermined transmission timing, the transmitting-receiving unit 3 generates pulse signals and transmits those pulse signals to the ultrasonic probe 2.

The transmitting-receiving unit 3 is electrically connected to the ultrasonic probe 2. With that, the transmitting-receiving unit 3 transmits pulse signals to the ultrasonic probe 2 and receives echo signals from the ultrasonic probe 2. More particularly, based on a predetermined waveform and a predetermined transmission timing, the transmitting-receiving unit 3 generates pulse signals and transmits those pulse signals to the ultrasonic probe 2. Moreover, the transmitting-receiving unit 3 performs operations such as amplification and filtering on received echo signals, performs A/D conversion of those echo signals to generate digital RF signals, and outputs those digital RF signals. Meanwhile, when the ultrasonic probe 2 is configured to have a plurality of ultrasonic transducers performing scanning in an electronic manner, the transmitting-receiving unit 3 is configured to include a multichannel circuit for performing beam synthesis corresponding to the ultrasonic transducers.

The processing unit 4 includes a frequency analyzing unit 41 that performs frequency analysis of echo signals by carrying out fast Fourier transformation (FFT) of the digital RF signals that are output by the transmitting-receiving unit 3; and includes a feature data extracting unit 42 that extracts feature data of the specimen by performing attenuation correction and approximation with respect to the frequency spectrum calculated by the frequency analyzing unit 41 so that there is a decrease in the contribution of attenuation, which occurs due to the reception depth and the frequency of ultrasonic sound waves being propagated.

The frequency analyzing unit 41 calculates a frequency spectrum with respect to each acoustic ray (line data) by performing fast Fourier transformation of an FFT data group having a predetermined volume of data. Depending on the tissue characterization of the specimen, the frequency spectrum demonstrates a different tendency. That is because of the fact that a frequency spectrum has a correlation with the size, the density, and the acoustic impedance of the specimen that serves as a scatterer which scatters the ultrasonic sound waves. Herein, for example, "tissue characterization" points to any one of a cancer, an endocrine tumor, a mucinous tumor, a normal tissue, and a vascular channel. If the specimen is pancreas, then chronic pancreatitis and autoimmune pancreatitis are also considered as tissue characterizations.

The feature data extracting unit 42 further includes an approximating unit 421, which performs approximation with respect to the frequency spectrum calculated by the frequency analyzing unit 41 and calculates pre-correction feature data that is the feature data prior to performing attenuation correction; and includes an attenuation correcting unit 422, which extracts feature data by performing attenuation correction with respect to the pre-correction feature data obtained by approximation by the approximating unit 421.

The approximating unit 421 performs linear approximation with respect to the frequency spectrum by means of regression analysis so as to extract feature data that characterizes the approximated linear expression. More particularly, by means of regression analysis, the approximating unit 421 calculates a gradient $a_0$ and an intercept $b_0$ of the linear expression, as well as calculates the intensity at a specific frequency within the frequency band of the frequency spectrum as the pre-correction feature data. In the first embodiment, it is assumed that, at the central frequency $f_{MID}=(f_{LOW}+$ $f_{HIGH})/2$, the approximating unit 421 calculates $c_0=a_0 f_{MID}+b_0$ as the intensity (Mid-band fit). However, that is only one example. Herein, the intensity points to any one parameter of parameters such as voltage, power, acoustic pressure, and acoustic energy.

Of the three components of feature data, the gradient $a_0$ has a correlation with the size of the scatterer that scatters the ultrasonic sound waves. Generally, it is thought that larger the scatterer, smaller is the value of the gradient. The intercept $b_0$ has a correlation with the size of the scatterer, the difference in acoustic impedances, and the density (consistency) of the scatterer. More particularly, it is thought that larger the scatterer, greater is the value of the intercept $b_0$; greater the acoustic impedance, greater is the value of the intercept $b_0$; and greater the density (concentration) of the scatterer, greater is the value of the intercept $b_0$. The intensity $c_0$ at the central frequency $f_{MID}$ (hereinafter, simply referred to as "intensity $c_0$") is an indirect parameter derived from the gradient $a_0$ and the intercept $b_0$, and represents the spectrum intensity at the center of the valid frequency band. Thus, it is thought that the intensity $c_0$ has a correlation not only with the size of the scatterer, the difference in acoustic impedances, and the density of the scatterer, but also with the luminosity values of B-mode images to a certain extent. Meanwhile, the approximation polynomial calculated by the feature data extracting unit 42 is not limited to a linear expression. Alternatively, it is also possible to use an approximation polynomial of second-order or more.

The following explanation is given for the correction performed by the attenuation correcting unit 422. An attenuation amount A of ultrasonic sound waves can be expressed as:

$$A = 2\alpha z f \quad (1)$$

where, $\alpha$ represents the attenuation rate, z represents the reception depth of ultrasonic sound waves, and f represents the frequency. As is clear from Equation (1), the attenuation amount A is proportional to the frequency f. Regarding a living body, the specific value of the attenuation rate $\alpha$ is in the range of 0 to 1.0 (dB/cm/MHz) and desirably is in the range of 0.3 to 0.7 (dB/cm/MHz), and is determined according to the organ to be observed. For example, if the organ to be observed is pancreas, then the attenuation rate $\alpha$ is set to 0.6 (dB/cm/MHz). Meanwhile, in the first embodiment, the configuration can also be such that the value of the attenuation rate $\alpha$ can be modified by an input from the input unit 6.

The attenuation correcting unit 422 corrects the pre-correction feature data (the gradient $a_0$, the intercept $b_0$, and the intensity $c_0$), which has been calculated by the approximating unit 421, in the following manner:

$$a = a_0 + 2\alpha z \quad (2)$$

$$b = b_0 \quad (3)$$

$$c = c_0 + 2\alpha z f_{MID} (= a f_{MID} + b) \quad (4)$$

As is clear from Equations (2) and (4) too, greater the reception depth of ultrasonic sound waves, greater is the amount of correction during the correction performed by the attenuation correcting unit 422. Meanwhile, with reference to Equation (3), the correction related to the intercept points to identical transformation. That is because of the fact that the intercept is a frequency component corresponding to the frequency 0 (Hz) and does not get attenuated.

The image processing unit 5 includes a B-mode image data generating unit 51 that generates B-mode image data from echo signals; and includes a feature-data image data generating unit 52 that generates feature-data image data containing information related to feature data.

The B-mode image data generating unit 51 generates B-mode image data by performing signal processing on digital signals using a known technology such as bandpass filtering, logarithmic conversion, gain processing, or contrast processing, and by performing data thinning according to the data step width that is decided in accordance to the display range of images in the display unit 7.

The feature-data image data generating unit 52 generates, in a temporally continuous manner, feature-data image data by referring to the B-mode image data generated by the B-mode image data generating unit 51 and by referring to the feature data extracted by the feature data extracting unit 42. More particularly, in a feature data space in which it is possible to set a coordinate system having at least some of the feature data extracted by the feature data extracting unit 42 as coordinate components, when a feature point of a frequency spectrum at a particular data position moves with the passage of time from a predetermined first type area closer to a second type area having low priority for image display than the first type area; the feature-data image data generating unit 52 sets a virtual feature point at a position that is far off from the second type area as compared to the position of the latest feature point and that is within or around the first type area, and assigns visual information corresponding to the virtual feature point to the same data position mentioned above so as to generate in a continuous manner the feature-data image data that contains information related to feature data. Herein, it is desirable that the first type area is set as an area corresponding to a tissue characterization of high importance such as cancer that should get detected during the observation.

In the first embodiment, with respect to the first type area, a virtual feature point is set as described above for the purpose of displaying a residual image. However, with respect to the second type area, no virtual feature point is set even in the case when a feature point of a frequency spectrum at a particular data position moves away from the second type area with the passage of time. In other words, the feature-data image data generating unit 52 performs residual image processing only with respect to the feature points present in the first type area in the feature data space.

The memory unit 8 includes a known-specimen information storing unit 81 that is used to store known specimen information including the feature data of known specimens; includes a window function storing unit 82 that is used to store a window function used during frequency analysis performed by the frequency analyzing unit 41; includes a correction information storing unit 83 that is used to store correction information which is referred to by the attenuation correcting unit 422 while performing attenuation correction; a feature-data-space information storing unit 84 that is used to store information related to feature data space which is set on the basis of the feature data of known specimens stored in the known-specimen information storing unit 81; and a feature data information storing unit 85 that is used to store information related to the feature data that is calculated as coordinate values of points in the feature data space which is stored in the feature-data-space information storing unit 84.

The known-specimen information storing unit 81 is used to store the feature data of frequency spectrums extracted for known specimens and the tissue characterizations of those known specimens in a corresponding manner. Herein, it is assumed that the feature data of a known specimen is extracted by performing an identical operation to that explained in the first embodiment. However, the feature data extracting operation for a known specimen need not be performed in the ultrasonic observation apparatus 1. Meanwhile, with respect to feature data of the frequency spectrum related to a known specimen, the known-specimen information storing unit 81 is also used to store the average and the standard deviation calculated for each group, which is classified on the basis of the information including the tissue characterization of that known specimen, along with all feature data of that known specimen. In the first embodiment, the average and the standard deviation of feature data of a frequency spectrum of ultrasonic reception signals reflect the changes at a cellular level such as enlargement or anomaly of the nucleus in the specimen or reflect the tissue-level changes such as fibrotic growth in the interstitium or substitution of parenchymal tissues with fibers. In consideration of the fact that unique values are indicated depending on the tissue characterization, the average and the standard deviation of feature data of the frequency spectrum of a known specimen are used to classify tissue characterizations.

The window function storing unit 82 is used to store at least one window function of the window functions such as Hamming, Hanning, and Blackman. The correction information storing unit 83 is used to store the information related to the conversion of Equations (2) to (4).

The feature-data-space information storing unit 84 is used to store a plurality of groups, which are obtained by classification on the basis of the feature data of a plurality of known specimens, and to store a representative point of each group as the information related to the feature data space that is set on the basis of the known specimen information stored in the known-specimen information storing unit 81. For example, a representative point can either be the average of feature data in the corresponding group or be the median point of feature data in the corresponding group.

Figure 2:
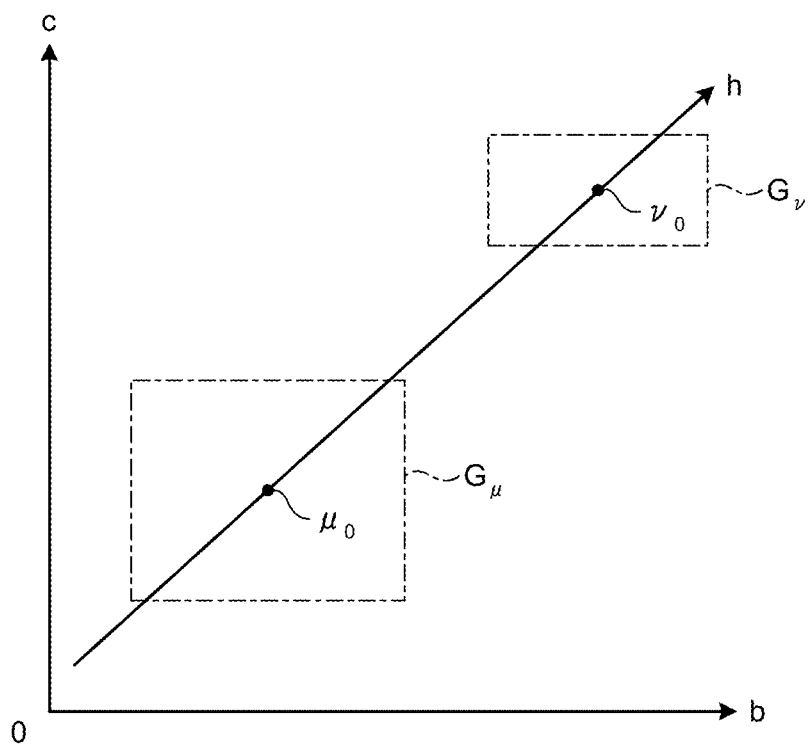
FIG. 2 is a diagram that schematically illustrates a configuration of a feature data space stored in the ultrasonic observation apparatus according to the first embodiment.

FIG. 2 is a diagram that schematically illustrates a configuration of the feature data space that is stored in the feature-data-space information storing unit 84. In the feature data space illustrated in FIG. 2, the horizontal axis represents the intercept b and the vertical axis represents the intensity c (see Equations (3) and (4)). Moreover, areas $G_\mu$ and $G_\nu$ represent groups in which a known specimen stored in the known-specimen information storing unit 81 has tissue characterization of $\mu$ and $\nu$, respectively. A point $\mu_0$ in the area $G_\mu$ is a representative point of the feature points that serve as elements of the area $G_\mu$ and a point $\nu_0$ in the area $G_\nu$ is a representative point of the feature points that serve as elements of the area $G_\nu$. In the first embodiment, the area $G_\mu$ is assumed to be the first type area (hereinafter, referred to as "residual image area") and the area $G_\nu$ is assumed to be the second type area.

The feature data information storing unit 85 stores therein feature points that are used at the time of calculating pixel values as visual information. Such feature points include the feature points extracted by the feature data extracting unit 42 as well as include residual image feature points that are virtual feature points determined according to the positions of feature points. Moreover, the feature data information storing unit 85 also stores, in a predetermined memory area thereof, a residual image area flag that takes different values depending on whether or not a feature point used at the time of calculating a pixel value is present in the residual image area. For example, when either a feature point present in the residual image area or a residual image feature point is used in calculating a pixel value, the feature data information storing unit 85 stores "1" as the value of the residual image area flag. On the other hand, when either a feature point present outside the residual image area or a residual image feature point is used in calculating a pixel value, the feature data information storing unit 85 stores "0" as the value of the residual image area flag.

Meanwhile, in FIG. 2, an h-axis (reference axis) is also illustrated that passes through the representative points $\mu_0$ and $\nu_0$ and that has the direction $\mu_0 \rightarrow \nu_0$ as the positive direction. When the feature-data image data generating unit 52 determines a pixel value of a pixel in a frame, the h-axis is used in determining whether to use the latest feature point or to use the pixel value of a residual image feature point that is already stored.

In the case illustrated in FIG. 2, in the feature data space, the two groups $G_\mu$ and $G_\nu$ are present in mutually exclusive areas. Thus, in the first embodiment, by classifying the groups with the feature data of the frequency spectrums, which is obtained during frequency analysis, serving as the index; it becomes possible to make distinction between mutually different groups. Particularly, in the first embodiment, attenuation correction is performed with respect to ultrasonic echo signals. Therefore, as compared to the case of not performing attenuation correction, each group in the feature data space can be obtained in a more distinctly separated state. Meanwhile, if the b-axis component and the c-axis component in the feature data space differ in scale by a large extent, it is desirable to appropriately perform weighting so that each distance contributes in a substantially equal manner.

Moreover, as the information about pixel values that is the visual information determined on a pixel-by-pixel basis, the feature-data-space information storing unit 84 stores therein the relationship between the points in the feature data space and the pixel values. For example, the feature-data-space information storing unit 84 stores therein the values of variables that constitute a color space and that are assigned to the intercept b and the intensity c. Herein, the color space points to a color system representing variables and representing the three attributes of light (hue, luminosity, and color intensity) of, for example, the RGB color system or a complementary color system.

Meanwhile, the memory unit 8 is put into practice with a ROM, which is used to store in advance operating programs of the ultrasonic observation apparatus 1 according to the first embodiment and to store programs for running a predetermined OS; and with a RAM, which is used to store operating parameters and data of each operation.

In the ultrasonic observation apparatus 1 having the above-mentioned functional configuration, the constituent elements other than the ultrasonic probe 2 are put into practice with a computer that includes a CPU for performing processing and control. The CPU in the ultrasonic observation apparatus 1 reads, from the memory unit 8, the information and various programs including the operating programs of the ultrasonic observation apparatus 1; and performs processing related to the operation method of the ultrasonic observation apparatus 1 according to the first embodiment.

The operating programs of the ultrasonic observation apparatus 1 can also be recorded in a computer readable recording medium such as a hard disk, a flash memory, a CD-ROM, a DVD-ROM, or a flexible disk for the purpose of distribution.

Figure 3:
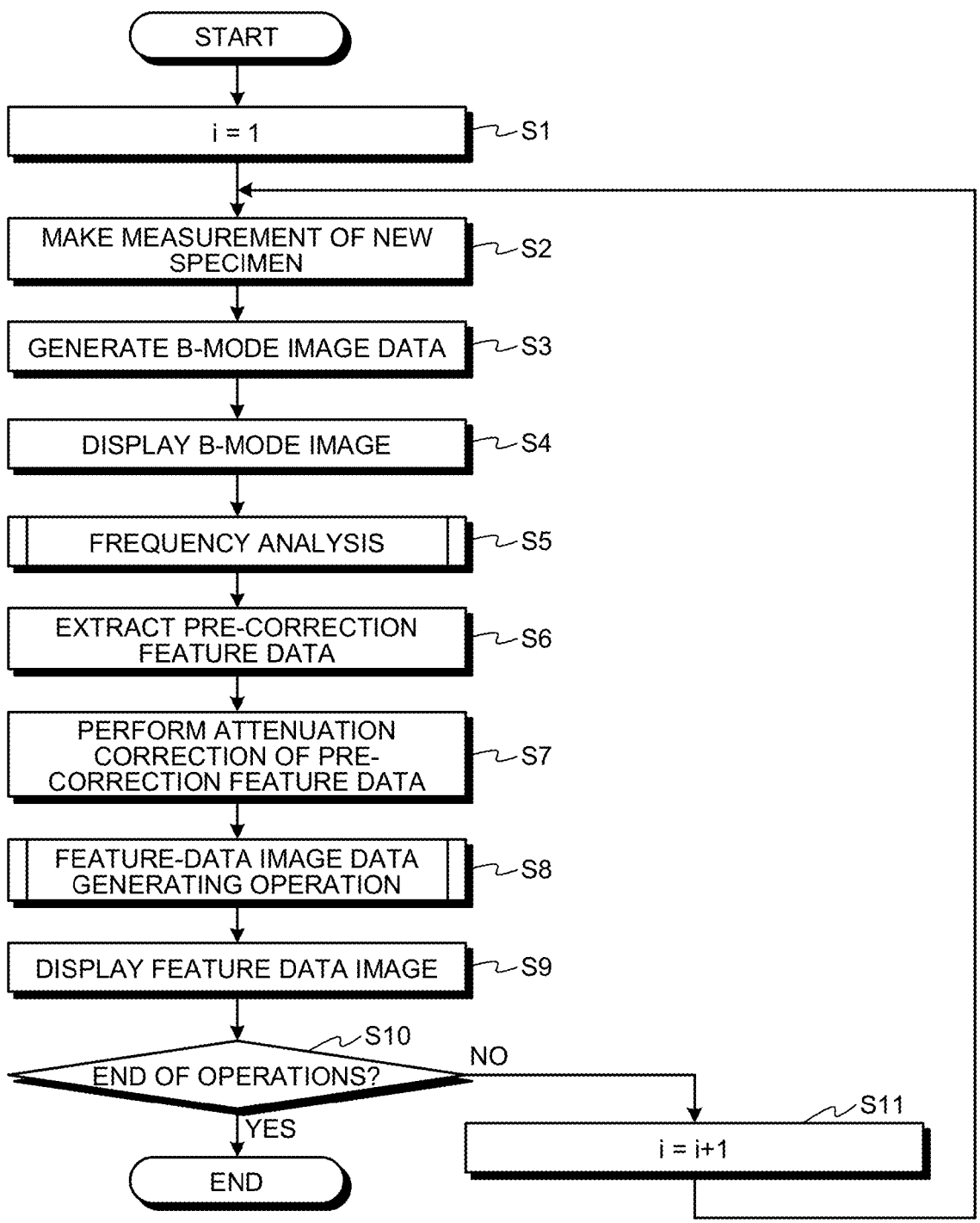
FIG. 3 is a flowchart for explaining an overview of the operations performed by the ultrasonic observation apparatus according to the first embodiment of the present invention.

FIG. 3 is a flowchart for explaining an overview of the operations performed by the ultrasonic observation apparatus 1 having the configuration explained above. In the flowchart illustrated in FIG. 3, the overview is given regarding the operations performed with respect to a single frame. In the following explanation, i (=1, 2, ... ) serves as the variable for identifying the frames.

With reference to FIG. 3, firstly, the ultrasonic observation apparatus 1 sets the variable i for identifying the frames to "1" (Step S1). Then, the ultrasonic observation apparatus 1 makes a measurement of a new specimen using the ultrasonic probe 2 (Step S2).

Subsequently, the B-mode image data generating unit 51 generates B-mode image data using echo signals for B-mode images output by the transmitting-receiving unit 3 (Step S3).

Figure 4:
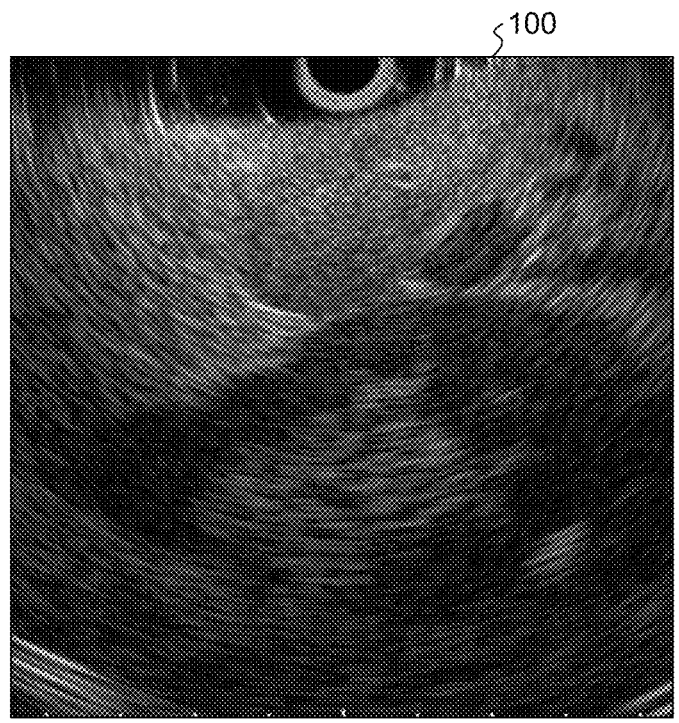
FIG. 4 is a diagram illustrating an example of a B-mode image displayed by a display unit of the ultrasonic observation apparatus according to the first embodiment of the present invention.

Subsequently, the control unit 9 performs control so that the display unit 7 displays a B-mode image corresponding to the B-mode image data generated by the B-mode image data generating unit 51 (Step S4). FIG. 4 is a diagram illustrating an example of a B-mode image displayed by the display unit 7. A B-mode image 100 illustrated in FIG. 4 is a grayscale image in which variables R (red), G (green), and B (blue), which are variables when the RGB color system is adopted as the color space, have identical values.

Figure 5:
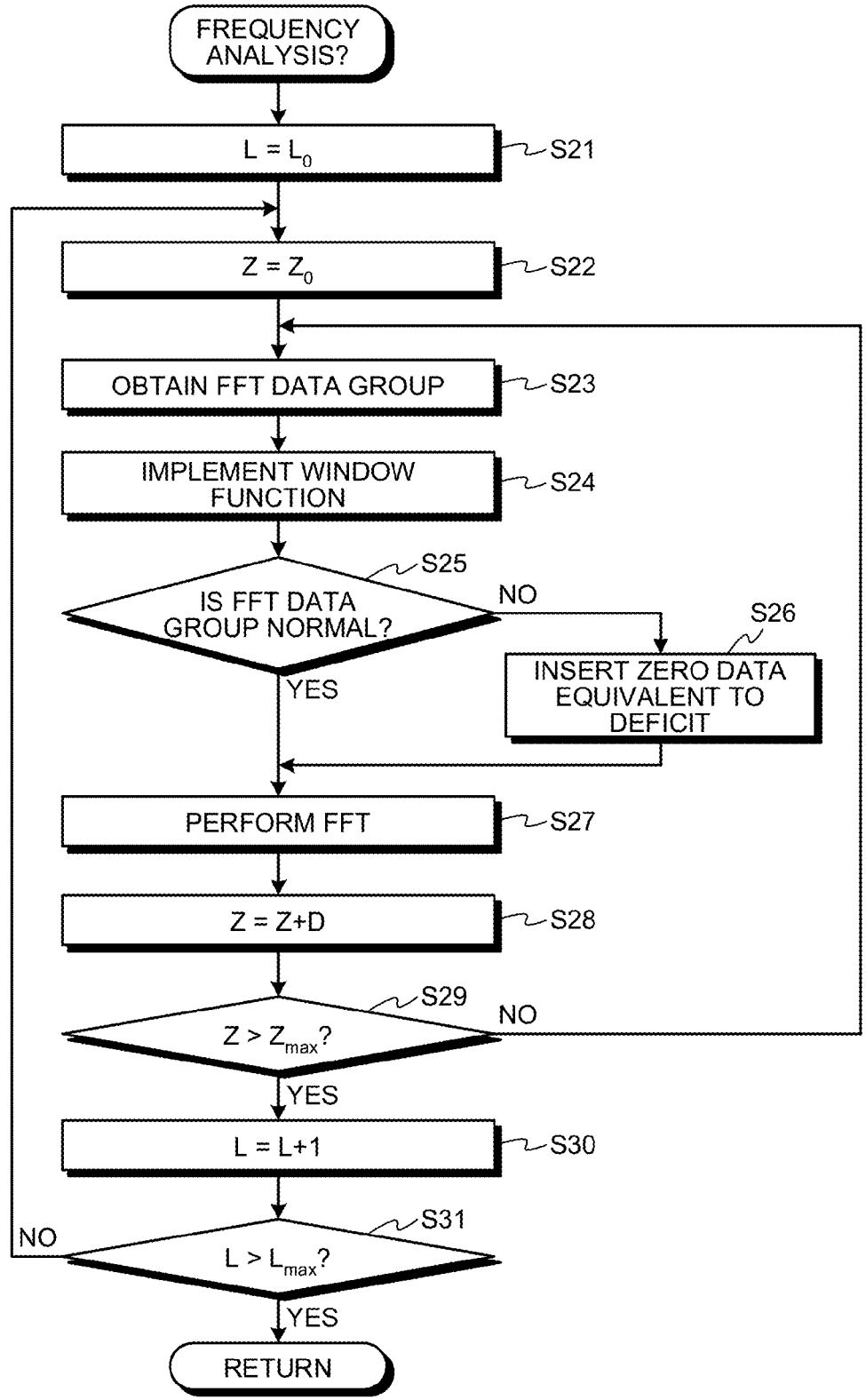
FIG. 5 is a flowchart for explaining an overview of the operations performed by a frequency analyzing unit of the ultrasonic observation apparatus according to the first embodiment of the present invention.

Then, the frequency analyzing unit 41 performs frequency analysis by means of FFT and calculates a frequency spectrum (Step S5). Herein, the operation performed by the frequency analyzing unit 41 at Step S5 is explained in detail with reference to a flowchart illustrated in FIG. 5. Firstly, the frequency analyzing unit 41 sets an acoustic ray number L of the acoustic ray to be initially analyzed to an initial value $L_0$ (Step S21). The initial value $L_0$ can be assigned, for example, to the acoustic ray received at the start by the transmitting-receiving unit 3 or to the acoustic ray corresponding to the boundary position on any one of the left and right sides of the area of concern set via the input unit 6.

Figure 6:
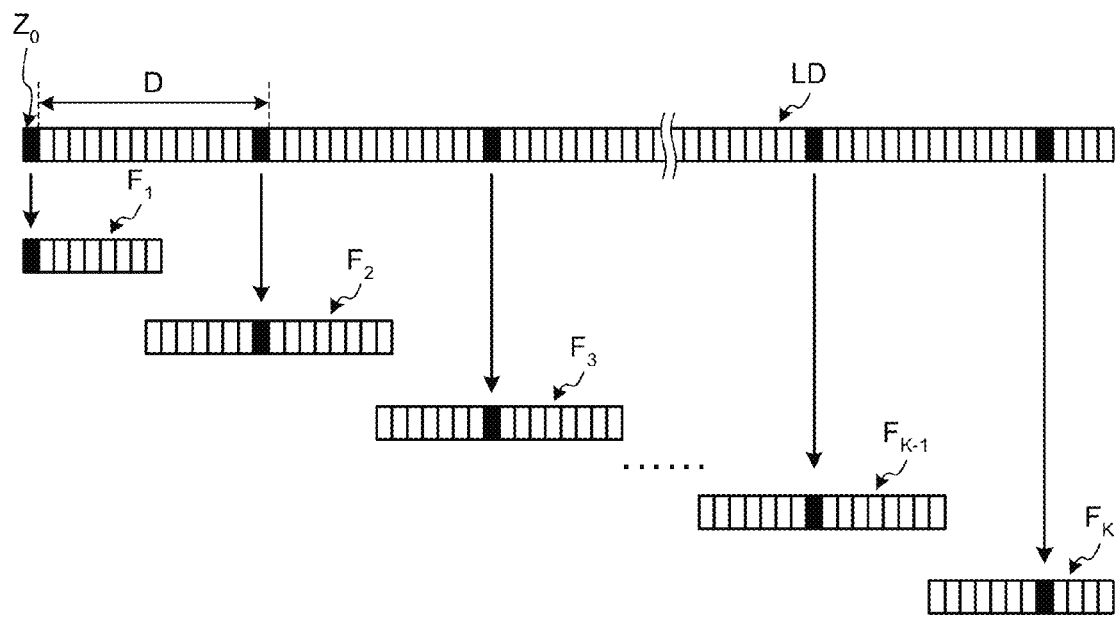
FIG. 6 is a diagram that schematically illustrates data arrangement of a single acoustic ray.

Then, the frequency analyzing unit 41 calculates the frequency spectrum of all data positions set on a single acoustic ray. Regarding that, firstly, the frequency analyzing unit 41 sets an initial value $Z_0$ of a data position Z (equivalent to reception depth) that is representative of a sequence of data groups (FFT data groups) obtained for the purpose of FFT (Step S22). FIG. 6 is a diagram that schematically illustrates data arrangement of a single acoustic ray. In an acoustic ray LD illustrated in FIG. 6, a white rectangle or a black rectangle represents a single set of data. The acoustic ray LD is discretized by time intervals corresponding to the sampling frequency (such as 50 MHz) used during A/D conversion performed by the transmitting-receiving unit 3. In FIG. 6, it is illustrated that the first set of data on the acoustic ray LD is set as the initial value $Z_0$ of the data position Z. Meanwhile, FIG. 6 is only an example, and the position of the initial value $Z_0$ can be set in an arbitrary manner. For example, the data position Z corresponding to the position at the top edge of the area of concern can be set as the initial value $Z_0$.

Then, the frequency analyzing unit 41 obtains the FFT data group at the data position Z (Step S23) and implements the window function, which is stored in the window function storing unit 82, to the FFT data group that has been obtained (Step S24). By implementing the window function to the FFT data group, it becomes possible to avoid discontinuity at the boundary in the FFT data group. As a result, artifacts can be prevented from occurring.

Subsequently, the frequency analyzing unit 41 determines whether or not the FFT data group at the data position Z is a normal data group (Step S25). Herein, it is necessary that the number of sets of data in an FFT data group is in power-of-two. In the following explanation, it is assumed that the number of sets of data in the FFT data group is $2^n$ (where n is a positive integer). When an FFT data group is normal, it means that the data position Z is the $2^{n-1}$-th position from the front of the FFT data group. In other words, when an FFT data group is normal, it means that there are $2^{n-1}-1$ (=N) number of sets of data prior to the data position Z, and there are $2^{n-1}$ (=M) number of sets of data subsequent to the data position Z. In the example illustrated in FIG. 6, FFT data groups $F_2$, $F_3$, and $F_{K-1}$ are normal data groups; while FFT data groups $F_1$ and $F_K$ are abnormal data groups. However, in FIG. 6, it is assumed that n=4 (N=7, M=8).

If the determination result of Step S25 indicates that the FFT data group at the data position Z is normal (Yes at Step S25), then the system control proceeds to Step S27 (described later).

If the determination result of Step S25 indicates that the FFT data group at the data position Z is not normal (No at Step S25), then the frequency analyzing unit 41 inserts zero data equivalent to the deficit and generates a normal FFT data group (Step S26). To the FFT data group that is determined to be not normal at Step S25, the window function is implemented prior to the addition of zero data. Hence, even if zero data is inserted, discontinuity in data does not occur. Once the operation at Step S26 is completed, the system control proceeds to Step S27.

Figure 7:
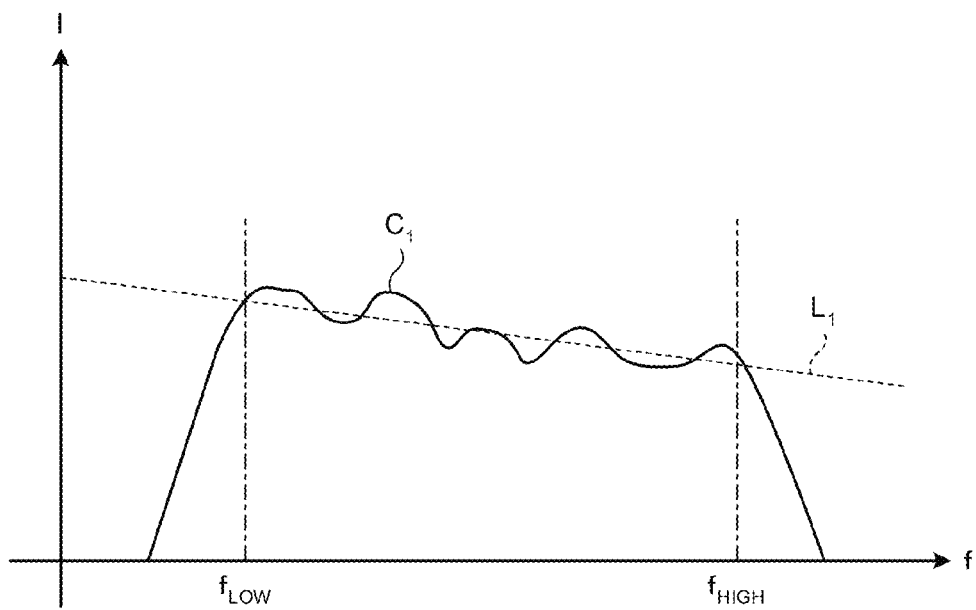
FIG. 7 is a diagram illustrating an example (first example) of the frequency spectrum calculated by the frequency analyzing unit of the ultrasonic observation apparatus according to the first embodiment of the present invention.
Figure 8:
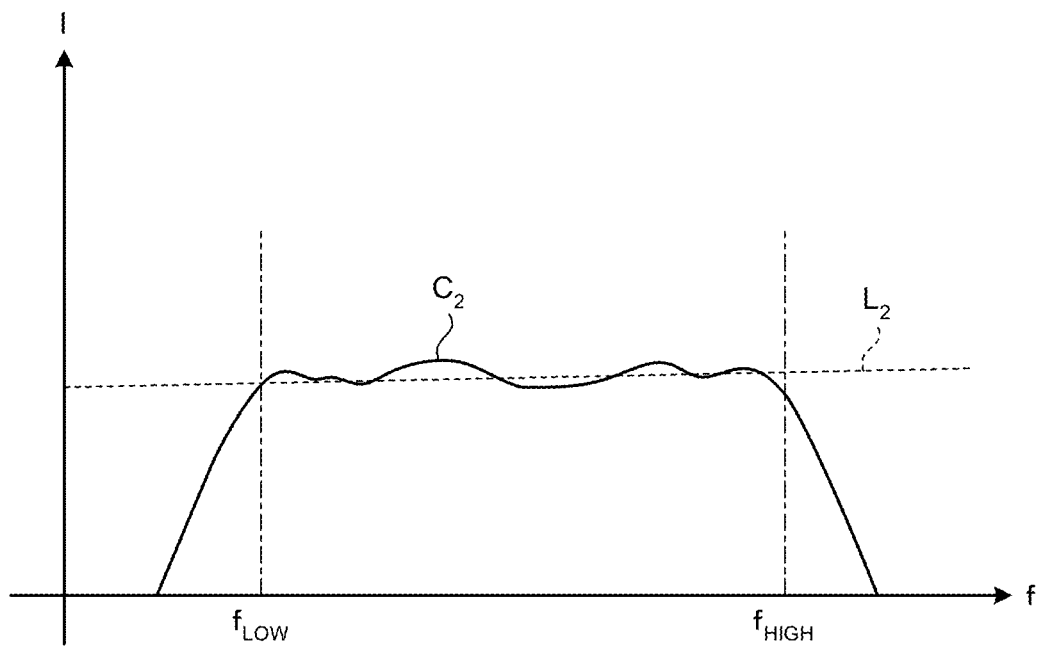
FIG. 8 is a diagram illustrating an example (second example) of the frequency spectrum calculated by the frequency analyzing unit of the ultrasonic observation apparatus according to the first embodiment of the present invention.

At Step S27, the frequency analyzing unit 41 performs FFT using the FFT data groups and obtains the frequency spectrum (Step S27). FIG. 7 and FIG. 8 are diagrams illustrating examples of the frequency spectrum calculated by the frequency analyzing unit 41. In FIG. 7 and FIG. 8, the horizontal axis f represents the frequency and the vertical axis I represents the intensity. In frequency spectrum curves $C_1$ and $C_2$ illustrated in FIG. 7 and FIG. 8, respectively; a lower limit frequency $f_{LOW}$ and a high limit frequency $f_{HIGH}$ of the frequency spectrum are parameters determined on the basis of the frequency band of the ultrasonic probe 2 and the frequency band of the pulse signals transmitted by the transmitting-receiving unit 3. For example, $f_{LOW}$ is equal to 3 MHz and $f_{HIGH}$ is equal to 10 MHz. Meanwhile, regarding a straight line $L_1$ illustrated in FIG. 7 and a straight line $L_2$ illustrated in FIG. 8, the explanation is given later while explaining the feature data extracting operation. In the first embodiment, curve lines and straight lines are formed of sets of discreet points. The same is the case in other embodiments described later.

Subsequently, the frequency analyzing unit 41 adds a predetermined data step width D to the data position Z, and calculates the data position Z at the FFT data group to be analyzed next (Step S28). Herein, it is desirable that the data step width D is matched with the data step width used at the time when the B-mode image data generating unit 51 generates B-mode image data. However, when the object is to reduce the amount of operations in the frequency analyzing unit 41, it is also possible to set the data step width D to a larger value than the data step width used by the B-mode image data generating unit 51. In FIG. 6, it is illustrated that D=15.

Subsequently, the frequency analyzing unit 41 determines whether or not the data position Z is greater than a final data position $Z_{max}$ (Step S29). Herein, the final data position $Z_{max}$ can be set to the data length of the acoustic ray LD or to the data position corresponding to the lower edge of the area of concern. If the determination result indicates that the data position Z is greater than the final data position $Z_{max}$ (Yes at Step S29), then the frequency analyzing unit 41 increments the acoustic ray number L by 1 (Step S30). On the other hand, if the determination result indicates that the data position Z is equal to or smaller than the final data position $Z_{max}$ (No at Step S29), then the system control returns to Step S23. In this way, with respect to a single acoustic ray LD, the frequency analyzing unit 41 performs FFT for $[\{(Z_{max}-Z_0)/D\}+1]$ (=K) number of FFT data groups. Herein, [X] represents the largest integer not exceeding X.

If the acoustic number L that has been incremented at Step S30 is greater than a final acoustic number $L_{max}$ (Yes at Step S31), then the system control returns to the main routine illustrated in FIG. 2. On the other hand, if the acoustic number L that has been incremented at Step S30 is equal to or smaller than the final acoustic number $L_{max}$ (No at Step S31), then the system control returns to Step S22.

In this way, the frequency analyzing unit 41 performs FFT for K number of times with respect to each of $(L_{max}-L_0+1)$ number of acoustic rays. For example, the final acoustic ray number $L_{max}$ can be assigned to the final acoustic ray received by the transmitting-receiving unit 3 or to the acoustic ray corresponding to the boundary position on any one of the left and right sides of the area of concern. In the following explanation, the total number of times for which the frequency analyzing unit 41 performs FFT with respect to all acoustic rays is $(L_{max}-L_0+1) \times K$ and is referred to as "P".

Subsequent to the frequency analyzing operation performed at Step S5 as described above, the approximating unit 421 performs, as an approximation operation, regression analysis of the P number of frequency spectrums calculated by the frequency analyzing unit 41 and extracts the pre-correction feature data (Step S6). More particularly, the approximating unit 421 performs regression analysis and calculates the linear expression for approximation of the frequency spectrums in the frequency band of $f_{LOW} < f < f_{HIGH}$; and then calculates the gradient $a_0$, the intercept $b_0$, and the intensity $c_0$, which characterize the linear expression, as the pre-correction feature data. The straight line $L_1$ illustrated in FIG. 7 and the straight line $L_2$ illustrated in FIG. 8 are regression lines obtained by performing regression analysis of the frequency spectrum curve $C_1$ and the frequency spectrum curve $C_2$, respectively, at Step S6.

Figure 9:
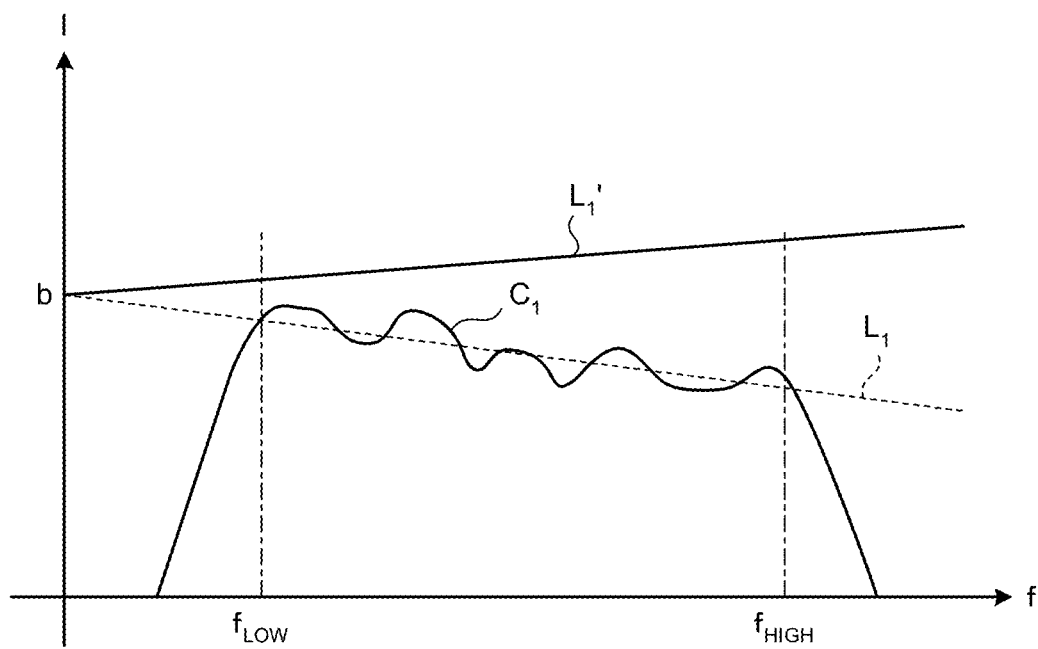
FIG. 9 is a diagram illustrating a new straight line that is determined from the feature data obtained upon performing attenuation correction of the feature data related to a straight line illustrated in FIG. 7.

Then, the attenuation correcting unit 422 performs attenuation correction of the pre-correction feature data extracted by the approximating unit 421 (Step S7). For example, when the data sampling frequency is 50 MHz, the time interval for data sampling is 20 (nsec). If the velocity of sound is assumed to be 1530 (m/sec), then the spacing among data sampling is equal to 1530 (m/sec)×20 (nsec)=0.0153 (mm). If "k" is assumed to be the number of data steps from the first set of data of the acoustic ray LD up to the data position of the FFT data group to be processed, then the data position Z thereof is equal to 0.0153 k (mm). The attenuation correcting unit 422 substitutes the value of the data position Z, which is obtained in the manner described above, in the reception depth z specified in Equations (2) to (4) mentioned above, and calculates the gradient a, the intercept b, and the intensity c. FIG. 9 is a diagram illustrating a straight line that is determined from the feature data obtained upon performing attenuation correction of the feature data related to the straight line $L_1$ illustrated in FIG. 7. A straight line $L_1'$ illustrated in FIG. 9 can be expressed as:

$$I = af + b = (a_0 + 2\alpha Z)f + b_0 \quad (5)$$

As is clear from Equation (5), as compared to the straight line $L_1$, the straight line $L_1'$ has a greater gradient with the same intercept value.

Figure 10:
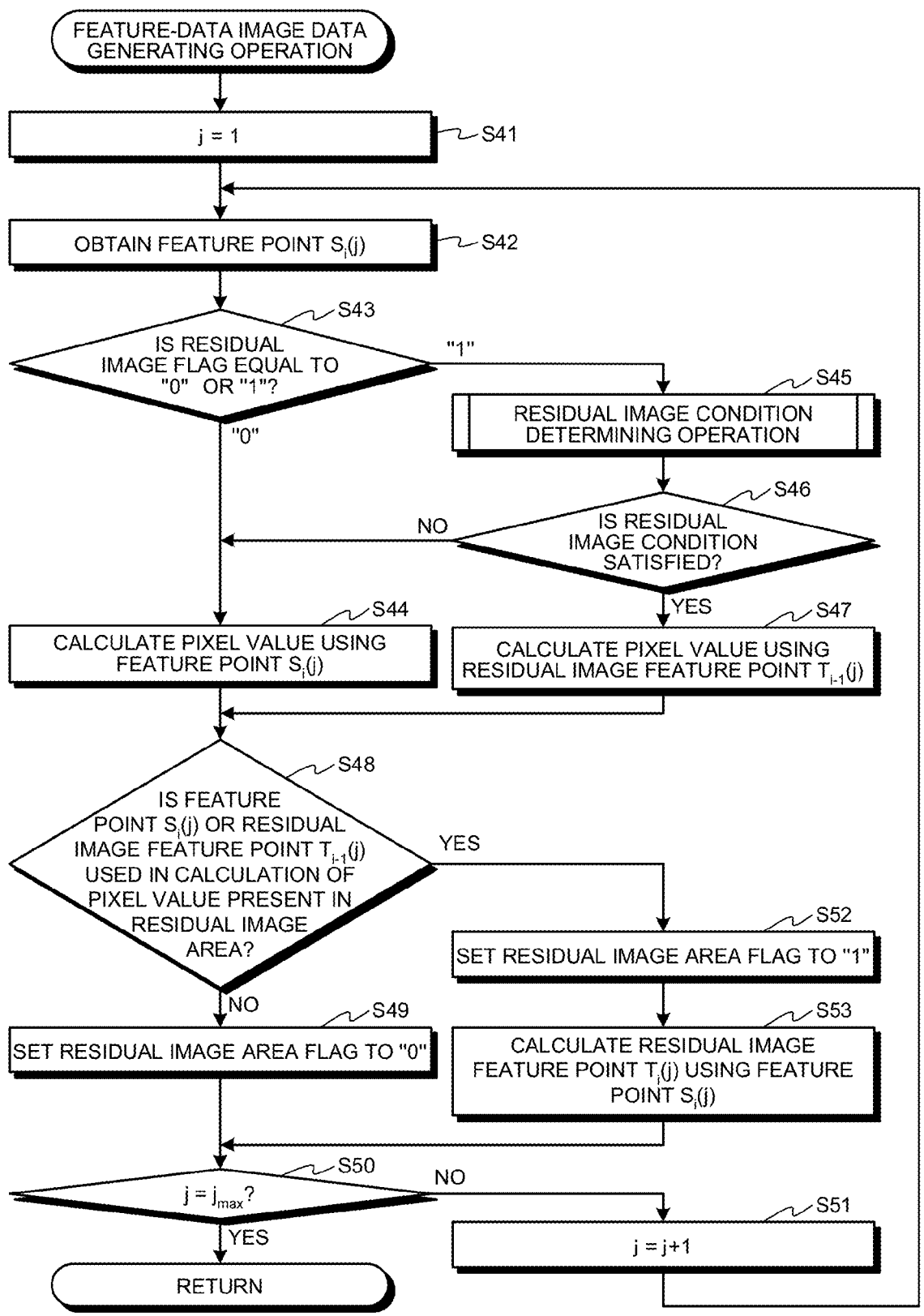
FIG. 10 is a flowchart for explaining an overview of a feature-data image data generating operation performed by a feature-data image data generating unit of the ultrasonic observation apparatus according to the first embodiment of the present invention.

Subsequently, the feature-data image data generating unit 52 generates feature-data image data (Step S8). FIG. 10 is a flowchart for explaining an overview of a feature-data image data generating operation performed by the feature-data image data generating unit 52. In the following explanation, j (=1, 2, ..., $j_{max}$) serves as the variable for identifying pixels included in a frame. Herein, for a pixel j of the frame at the i-th number (i-th frame), an intercept $b_i(j)$ and an intensity $c_i(j)$ serve as the feature data; and the set $(b_i(j), c_i(j))$ is called a feature point and is referred to as $S_i(j)$.

With reference to FIG. 10, firstly, the feature-data image data generating unit 52 sets the variable j for pixel identification to "1" (Step S41).

Then, the feature-data image data generating unit 52 obtains a feature point (first feature point) $S_i(j)$ that has been extracted by the feature data extracting unit 42 (Step S42), reads the residual image area flag of that feature point $S_i(j)$ from the feature-data-space information storing unit 84, and determines the value of the residual image area flag (Step S43). If the residual image area flag is "0" (0 at Step S43), then the feature-data image data generating unit 52 calculates the pixel value of the pixel j using the feature point $S_i(j)$ (Step S44).

On the other hand, if the residual image area flag of the feature point $S_i(j)$ is "1" (1 at Step S43), then the feature-data image data generating unit 52 determines whether or not a residual image condition is satisfied (Step S45).

Figure 11:
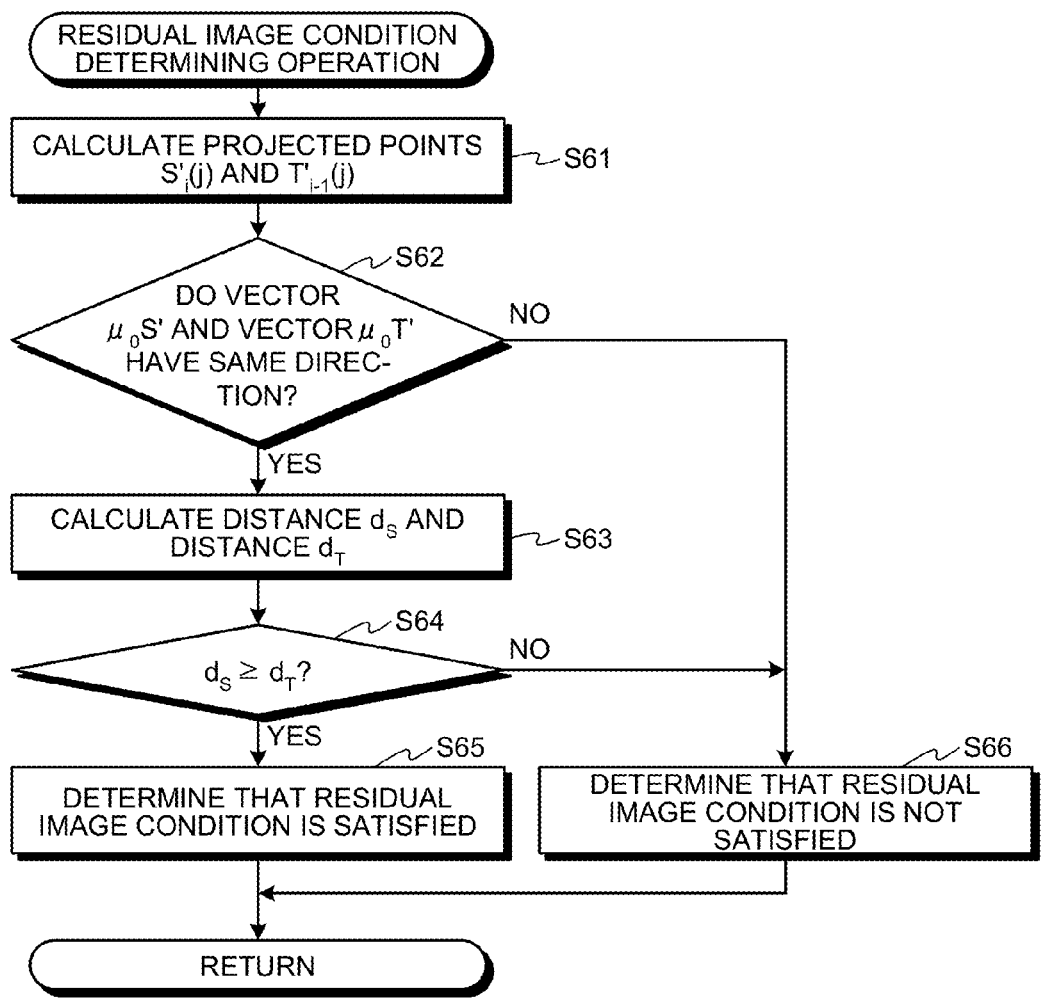
FIG. 11 is a flowchart for explaining an overview of a residual image condition determining operation performed by the feature-data image data generating unit of the ultrasonic observation apparatus according to the first embodiment of the present invention.

FIG. 11 is a flowchart for explaining an overview of a residual image condition determining operation. With reference to FIG. 11, the feature-data image data generating unit 52 calculates the coordinates of a projected point $S'_i(j)$, which is the point obtained when the feature point $S_i(j)$ is projected on the h-axis in the feature data space, as well as calculates the coordinates of a projected point $T'_{i-1}(j)$, which is the point obtained when a residual image feature point (second feature point) $T_{i-1}(j)$ is projected on the h-axis in the feature data space (Step S61).

Then, the feature-data image data generating unit 52 determines whether or not a vector $\mu_0 S'$, which has the representative point $\mu_0$ as the start point and the projected point $S'_i(j)$ as the end point, has the same direction as a vector $\mu_0 T'$, which has the representative point $\mu_0$ as the start point and the projected point $T'_{i-1}(j)$ as the end point (Step S62). If the determination result indicates that the two vectors $\mu_0 S'$ and $\mu_0 T'$ have the same direction (Yes at Step S62), then the feature-data image data generating unit 52 calculates a distance $d_S$ between the projected point $S'_i(j)$ and the representative point $\mu_0$ as well as calculates a distance $d_T$ between the projected point $T'_{i-1}(j)$ and the representative point $\mu_0$ (Step S63).

Figure 12:
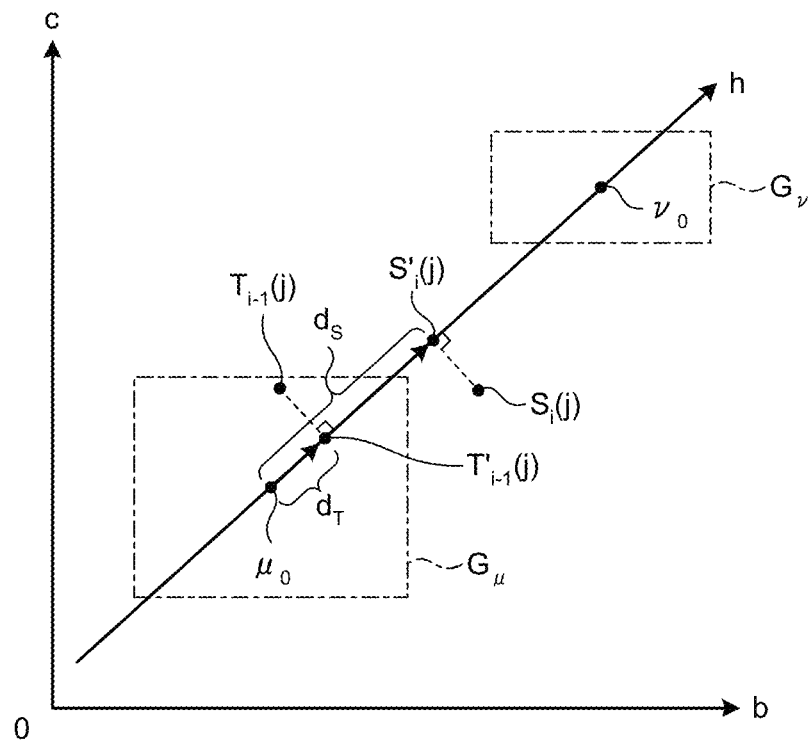
FIG. 12 is a diagram that schematically illustrates a case during the residual image condition determining operation, which is performed by the feature-data image data generating unit of the ultrasonic observation apparatus according to the first embodiment of the present invention, when it is determined that a residual image condition is satisfied.

Subsequently, the feature-data image data generating unit 52 compares the distance $d_S$ with the distance $d_T$ (Step S64). If the comparison result indicates that the distance $d_S$ is equal to or greater than the distance $d_T$ (Yes at Step S64), then the feature-data image data generating unit 52 determines that the residual image condition is satisfied (Step S65), and the system control proceeds to Step S46. FIG. 12 is a diagram illustrating a condition of the feature data space when the two vectors $\mu_0 S'$ and $\mu_0 T'$ have the same direction and when that the distance $d_S$ is equal to or greater than the distance $d_T$. In this case, as compared to the projected point $T'_{i-1}(j)$, the projected point $S'_i(j)$ is closer to the representative point $v_0$ of the area $G_v$. Thus, if the pixel value is set on the basis of the residual image feature point $T_{i-1}(j)$, then it becomes possible to display an image that is close to the display form when the feature data is present in the area $G_\mu$. In other words, if the image is displayed by replacing the pixel value corresponding to the feature point $S_i(j)$ with the pixel value corresponding to the residual image feature point $T_{i-1}(j)$, which is a virtual feature point; then it becomes possible to display an image that is close to the display form when the feature data is present in the area $G_\mu$.

Figure 13:
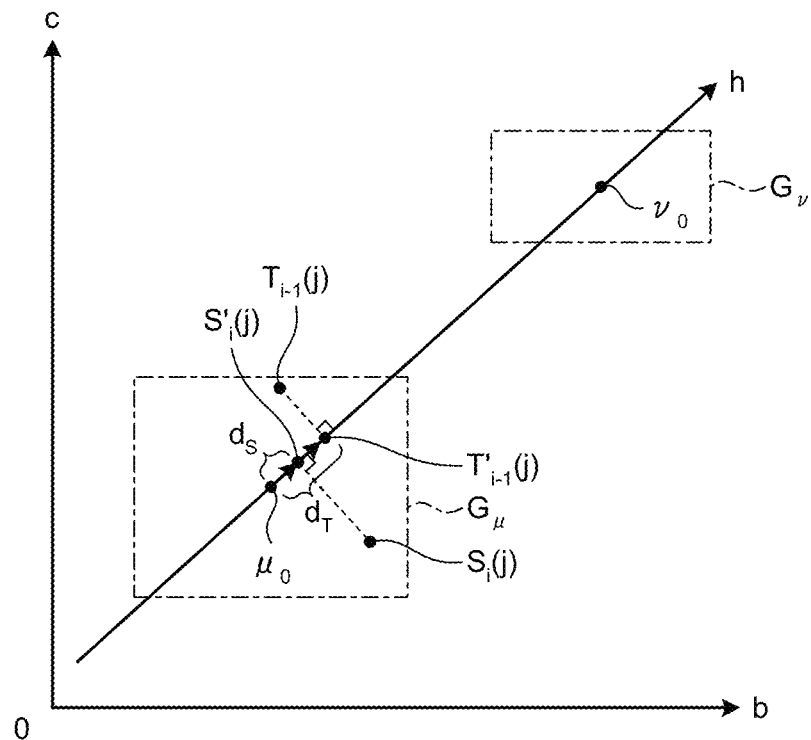
FIG. 13 is a diagram that schematically illustrates an exemplary case (first example) during the residual image condition determining operation, which is performed by the feature-data image data generating unit of the ultrasonic observation apparatus according to the first embodiment of the present invention, when it is determined that the residual image condition is not satisfied.

Meanwhile, if the comparison result at Step S64 indicates that the distance $d_S$ is smaller than the distance $d_T$ (No at Step S64), then the feature-data image data generating unit 52 determines that the residual image condition is not satisfied (Step S66), and the system control proceeds to Step S46. FIG. 13 is a diagram illustrating a condition of the feature data space when the two vectors $\mu_0 S'$ and $\mu_0 T'$ have the same direction and when that the distance $d_S$ is smaller than the distance $d_T$. In this case, as compared to the projected point $T'_{i-1}(j)$, the projected point $S'_i(j)$ is distantly-positioned from the representative point $v_0$ of the group $G_v$. Thus, if the pixel value is set on the basis of the feature point $S_i(j)$ present in the area $G_\mu$, it becomes possible to display an image having pixel values assigned thereto based on more correct positions in the area $G_\mu$.

Figure 14:
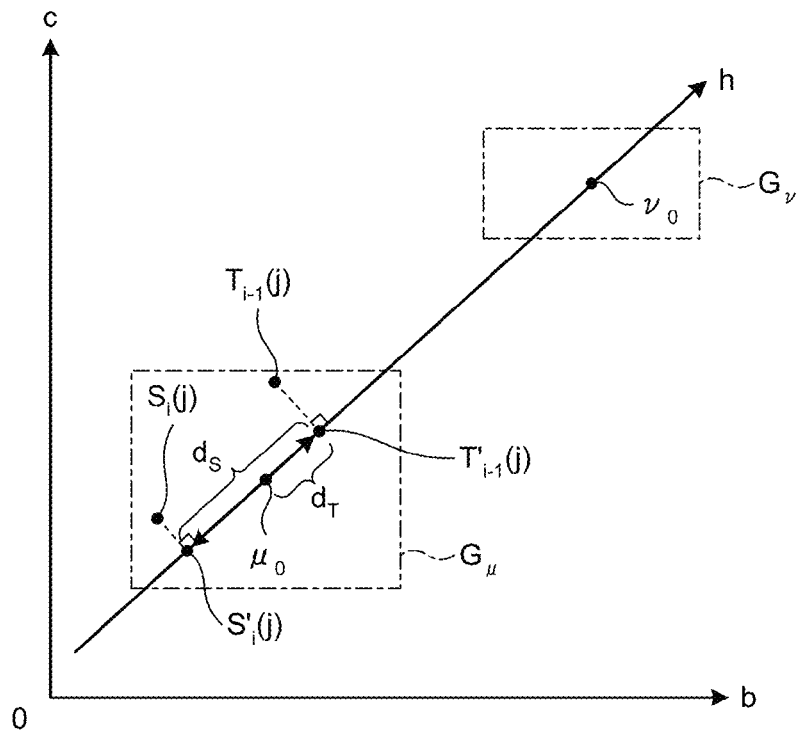
FIG. 14 is a diagram that schematically illustrates an exemplary case (second example) during the residual image condition determining operation, which is performed by the feature-data image data generating unit of the ultrasonic observation apparatus according to the first embodiment of the present invention, when it is determined that the residual image condition is not satisfied.

Meanwhile, if the determination result indicates that the two vectors $\mu_0 S'$ and $\mu_0 T'$ do not have the same direction (No at Step S62), then the system control proceeds to Step S66. FIG. 14 is a diagram illustrating a condition of the feature data space when the two vectors $\mu_0 S'$ and $\mu_0 T'$ do not have the same direction. In this case, as compared to the projected point $T'_{i-1}(j)$, the projected point $S'_i(j)$ is distantly-positioned from the representative point $v_0$ of the group $G_v$. Thus, if the pixel value is set on the basis of the feature point $S_i(j)$ present in the area $G_\mu$, it becomes possible to display an image having pixel values assigned thereto based on more correct positions in the area $G_\mu$.

Returning to the explanation with reference to FIG. 10, if the result of the residual image condition determining operation at Step S45 indicates that the residual image condition is satisfied (Yes at Step S46), then the feature-data image data generating unit 52 calculates a pixel value using the residual image feature point $T_{i-1}(j)$ (Step S47). On the other hand, if the residual image condition is not satisfied (No at Step S46); then the system control proceeds to Step S44.

After the operation at Step S44 or Step S47 is completed, the feature-data image data generating unit 52 determines whether the feature point $S_i(j)$ or the residual image feature point $T_{i-1}(j)$ used in calculating the pixel value is present in the residual image area (Step S48). When the feature point $S_i(j)$ or the residual image feature point $T_{i-1}(j)$ is not present in the residual image area (No at Step S48), then the feature-data image data generating unit 52 sets the residual image area flag to "0" (Step S49).

Then, if the variable j for identifying pixel values has reached a maximum value $j_{max}$ (Yes at Step S50), the feature-data image data generating unit 52 ends the feature-data image data generating operation. In contrast, if the variable j for identifying pixel values is smaller than the maximum value $j_{max}$ (No at Step S50), the feature-data image data generating unit 52 increments the variable j by 1 (Step S51), and the system control returns to Step S42. Herein, the increment in the variable j means nothing more than a change in the pixel to be processed. Thus, there is no change in variables such as the feature point and the residual image feature point that are assigned to the pixels on an individual basis.

Figure 15:
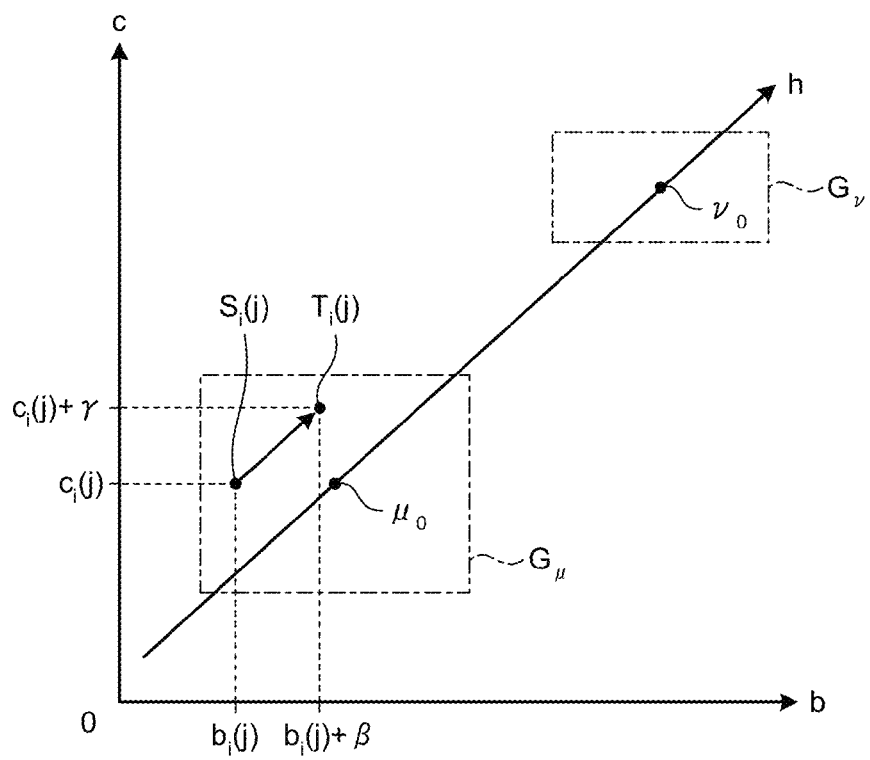
FIG. 15 is a diagram illustrating an overview of a method of calculating a residual image feature point in the ultrasonic observation apparatus according to the first embodiment of the present invention.

The following explanation is given for the case when, at Step S48, the feature point $S_i(j)$ or the residual image feature point $T_{i-1}(j)$ is present in the residual image area (Yes at Step S48). In this case, the feature-data image data generating unit 52 sets the residual image area flag to "1" (Step S52), calculates a residual image feature point $T_i(j)$ using the feature point $S_i(j)$, and stores the residual image feature point $T_i(j)$ in the feature-data-space information storing unit 84 (Step S53). Then, the system control proceeds to Step S50. FIG. 15 is a diagram illustrating an overview of the method of calculating the residual image feature point $T_i(j)$. As illustrated in FIG. 15, the residual image feature point $T_i(j)$ is obtained by shifting each component of the feature point $S_i(j)$ by a predetermined amount. That is, the residual image feature point $T_i(j)$ is set to have the coordinates $(b_i(j)+\beta, c_i(j)+\gamma)$, where "$\beta$" and "$\gamma$" are positive constant numbers. The residual image feature point $T_i(j)$ is set as a value that is closer to the representative point $v_0$ of the group $G_v$ as compared to the feature point $S_i(j)$. Meanwhile, in FIG. 15, although the direction of shifting is illustrated to be parallel to the h-axis, it is only an exemplary case.

Figure 16:
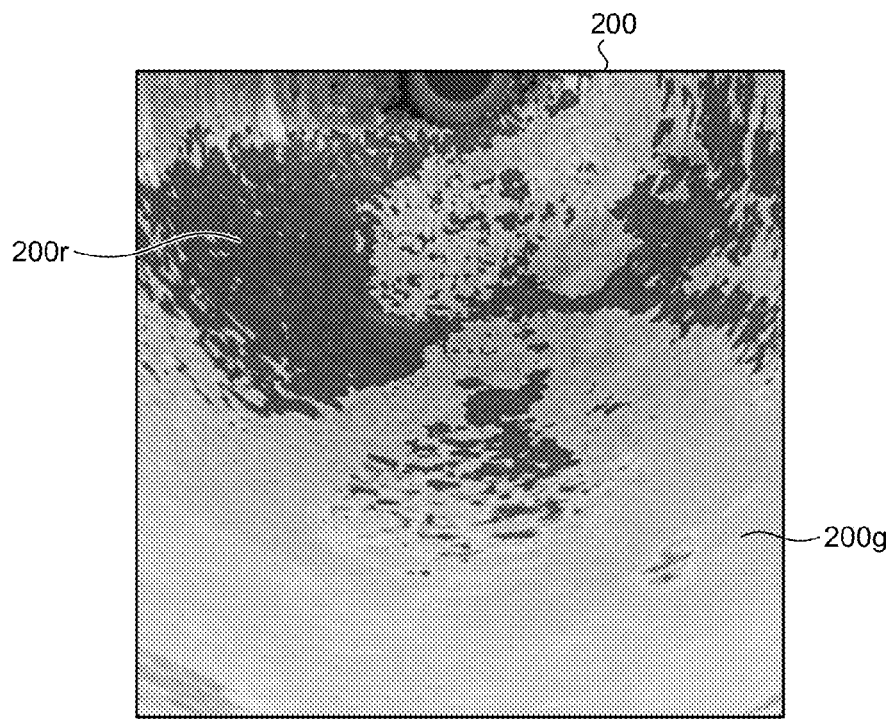
FIG. 16 is a diagram illustrating an example of a feature data image displayed by the display unit of the ultrasonic observation apparatus according to the first embodiment of the present invention.
Figure 17:
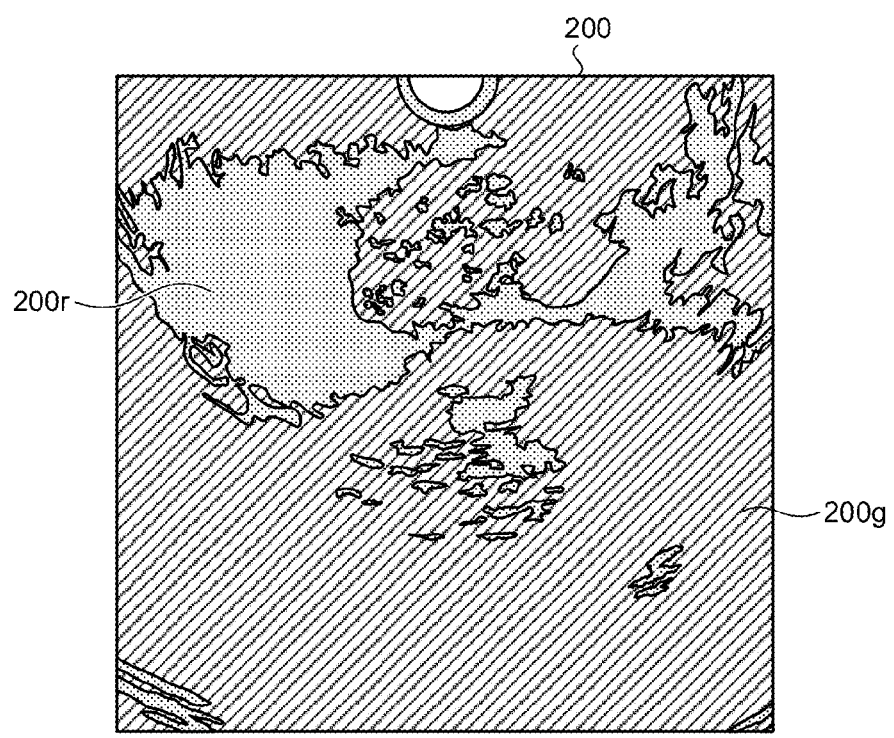
FIG. 17 is a diagram that schematically illustrates a black-and-white image of the image illustrated in FIG. 16.

Subsequently, the display unit 7 displays a feature data image generated by the feature-data image data generating unit 52 (Step S9). FIG. 16 is a diagram illustrating an example of a feature data image displayed by the display unit 7. FIG. 17 is a diagram that schematically illustrates a black-and-white image of the image illustrated in FIG. 16. As compared to the B-mode image 100, a feature data image 200 illustrated in FIG. 16 and FIG. 17 is colorized in such a manner that there is a clear difference in colors according to the groups. The feature data image 200 can be broadly divided into a greenish area 200g and a reddish area 200r, with the boundary portion between those two areas displayed in a yellowish color (not illustrated in FIG. 17). As illustrated in FIG. 16, it is not the case that each area is made of only a single color. For example, the greenish area 200g is an area including pixels having colors close to the green color. Similarly, the reddish area 200r is an area including pixels having colors close to the red color. Thus, the observer who observes the feature data image 200 can clearly recognize the differences in groups, that is, can clearly recognize the differences in tissue characterizations. Meanwhile, the control unit 9 can also instruct the display unit 7 to display side-by-side a feature data image and a B-mode image. With that, the differences in the two images become recognizable on the same screen.

Subsequently, when an instruction signal for instructing the end of operations is input via the input unit 6 (Yes at Step S10), then the ultrasonic observation apparatus 1 ends the sequence of operations. On the other hand, if no instruction signal for instructing the end of operations is input via the input unit 6 (No at Step S10), then the ultrasonic observation apparatus 1 increments the variable i for identifying the frames by 1 (Step S11), and the system control returns to Step S2.

Figure 18:
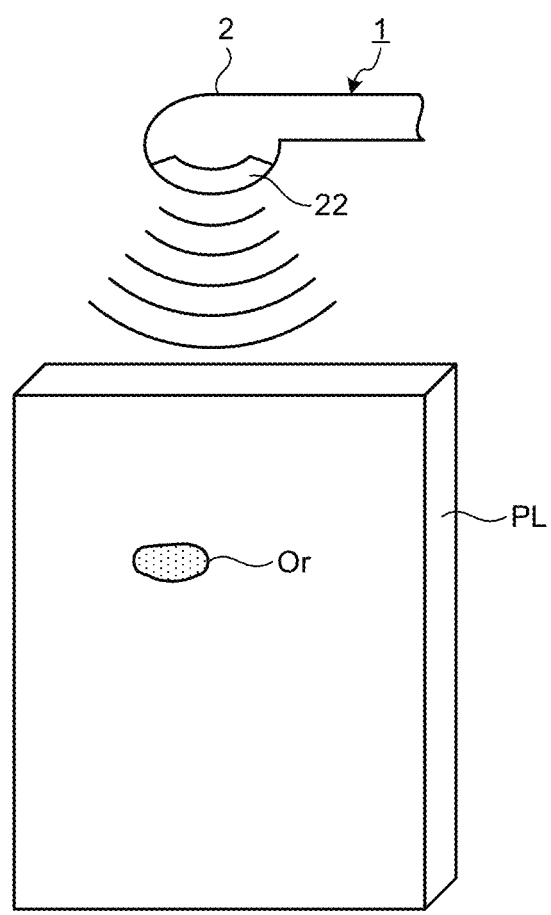
FIG. 18 is a diagram that schematically illustrates a condition observed by the ultrasonic observation apparatus according to the first embodiment of the present invention.

Explained below is the effect of the first embodiment. Generally, as a target for observation, the ultrasonic observation apparatus 1 observes a slice plane having a uniform thickness inside the specimen. FIG. 18 is a diagram that schematically illustrates a condition observed by the ultrasonic observation apparatus 1. As illustrated in FIG. 18, the ultrasonic probe 2 is disposed at the leading end of the ultrasonic observation apparatus 1 and includes a vibrator group 22 made of a plurality of vibrators, each of which sequentially sends ultrasonic sound waves at a predetermined timing. Such ultrasonic sound waves reach a slice plane PL having a uniform thickness inside the specimen. Meanwhile, in FIG. 18, although the slice plane PL is illustrated as a rectangular solid, it is only for the sake of convenience. In practice, the shape of the slice plane PL varies according to the portion to be observed in a specimen.

Under the condition illustrated in FIG. 18, in a typical ultrasonic observation apparatus, there are times when the relative position relationship between the ultrasonic probe 2 and the specimen changes due to the movement of at least either one of them. In such a case, the slice plane PL that is the target for observation also changes. If the slice plane PL changes, a situation may occur in which a tissue Or that is present in the specimen and that is observed in the first frame is not observed in subsequent frames. The reason for the occurrence of such a situation can be that the tissue Or observed in the first frame is either very small or is distantly-positioned from the ultrasonic probe.

Figure 19:
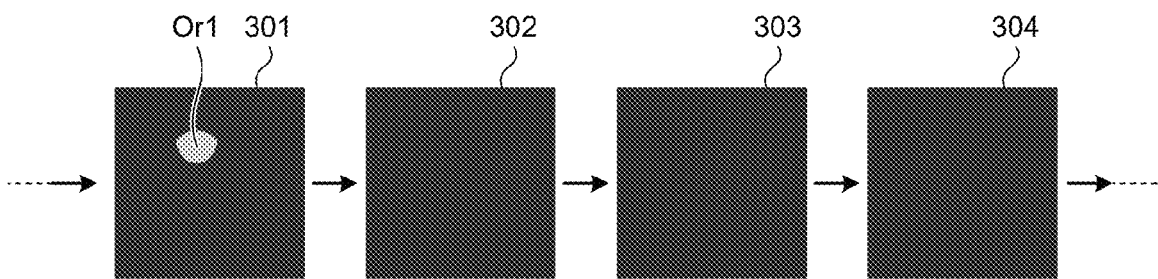
FIG. 19 is a diagram that schematically illustrates a display example (first example) of feature data images displayed by a display unit of a typical ultrasonic observation apparatus when the relative position relationship between an ultrasonic probe and a specimen changes with time.

FIG. 19 is a diagram that schematically illustrates a display example (first example) of feature data images displayed by a display unit of a typical ultrasonic observation apparatus when the relative position relationship between the ultrasonic probe and the specimen changes with time. In the case illustrated in FIG. 19, a tissue Or1 displayed in a first feature data image 301 completely disappears from feature data images 302, 303, and 304 that are displayed in that order after the first feature data image 301.

Figure 20:
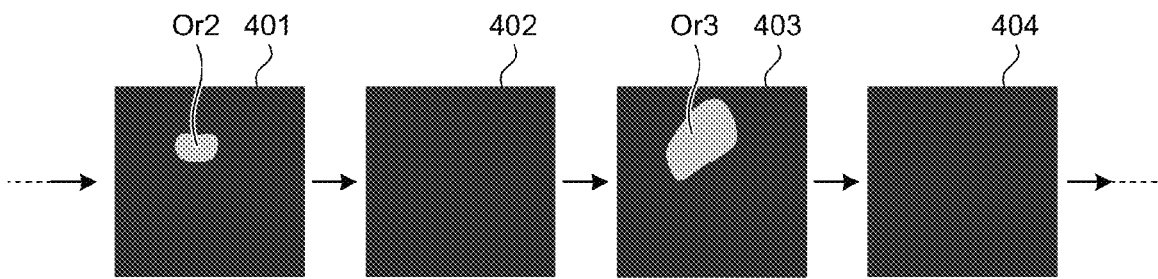
FIG. 20 is a diagram that schematically illustrates a display example (second example) of feature data images displayed by a display unit of a typical ultrasonic observation apparatus when the relative position relationship between the ultrasonic probe and the specimen changes with time.

FIG. 20 is a diagram that schematically illustrates a display example (second example) of feature data images displayed by a display unit of a typical ultrasonic observation apparatus when the relative position relationship between the ultrasonic probe and the specimen changes with time. In the case illustrated in FIG. 20, a tissue Or2 displayed in a first feature data image 401 disappears from a feature data image 402 displayed subsequently. Besides, in a feature data image 403 that is displayed after the feature data image 402, a tissue Or3 having a different shape than the tissue Or2 is displayed. However, that tissue Or3 disappears from a feature data image 404 displayed subsequently.

As illustrated in FIG. 19 and FIG. 20, in a typical ultrasonic observation apparatus, the relative position relationship between the ultrasonic probe and the specimen changes with time. Because of that, it is not possible to observe a desired tissue over an extended period of time.

Figure 21:
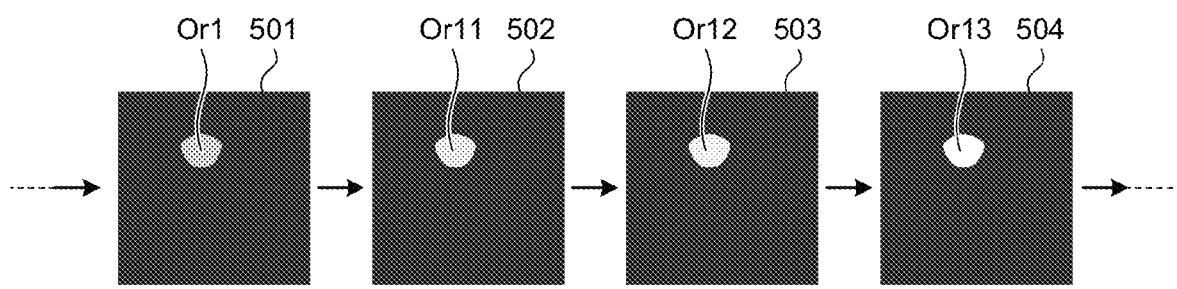
FIG. 21 is a diagram that schematically illustrates a display example of feature data images displayed under the same condition as that illustrated in FIG. 19 by the display unit of the ultrasonic observation apparatus according to the first embodiment of the present invention.
Figure 22:
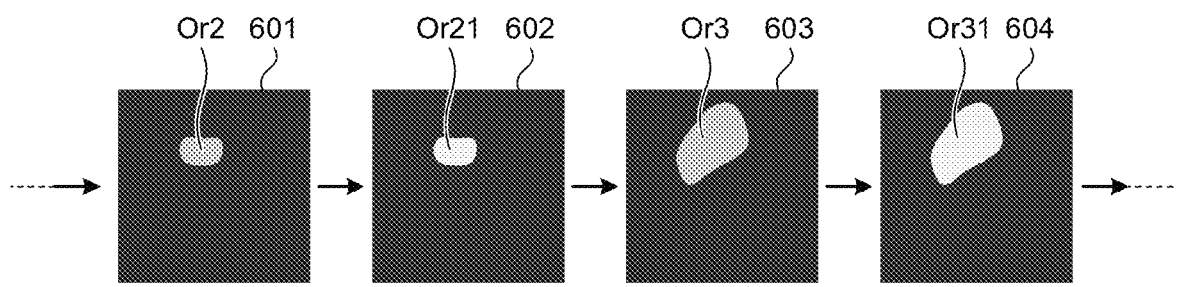
FIG. 22 is a diagram that schematically illustrates a display example of feature data images displayed under the same condition as that illustrated in FIG. 20 by the display unit of the ultrasonic observation apparatus according to the first embodiment of the present invention.

FIG. 21 and FIG. 22 are diagrams for explaining the effect of the operations performed by the ultrasonic observation apparatus 1 according to the first embodiment. FIG. 21 is a diagram that schematically illustrates a display example displayed by the display unit 7 under the same condition as that illustrated in FIG. 19. In the case illustrated in FIG. 21, in an identical manner to FIG. 19, the tissue Or1 is observed only at the point of time of capturing a feature data image 501 that is displayed initially. However, as a result of performing the operations described above, in feature data images 502, 503, and 504 that are displayed after the feature data image 501; residual images Or11, Or12, and Or13 of the same shape are respectively displayed at the same position as the position of the tissue Or1. Although the residual images Or11, Or12, and Or13 have a similar display color to the display color of the tissue Or1, there is a slight difference in the display color. That is because, in the feature data space, the feature points corresponding to pixels in the area constituting each residual image are different than the feature points corresponding to the pixels in the tissue Or1.

FIG. 22 is a diagram that schematically illustrates a display example displayed by the display unit 7 under the same condition as that illustrated in FIG. 20. In the case illustrated in FIG. 22, the tissue Or2 is observed only at the point of time of capturing a feature data image 601 that is displayed initially. In FIG. 22, in a feature data image 602 corresponding to the feature data image 402 illustrated in FIG. 20, a residual image Or21 of the tissue Or2 is displayed. Moreover, in a feature data image 603 that is displayed subsequent to the feature data image 602, the tissue Or3 is displayed in an identical manner to the tissue Or3 displayed in the feature data image 403 illustrated in FIG. 20. In a feature data image 604 that is displayed subsequent to the feature data image 603, a residual image Or31 of the tissue Or3 is displayed. In the case illustrated in FIG. 22, the display color of the tissue Or2 is different than the display color of the residual image Or21, and the display color of the tissue Or3 is different than the display color of the residual image Or31.

In this way, in the first embodiment, while displaying feature data images, even in the frames in which tissues did not get displayed in the past, a residual image are drawn based on the tissue or based on the residual image displayed immediately before. Hence, even if a high-priority tissue is not observed in a particular frame; the image in the corresponding previous frame can be used to display a residual image, thereby making it possible to display the desired tissue over an extended period of time. As a result, the user can observe the desired images in a continuous manner.

Figure 23:
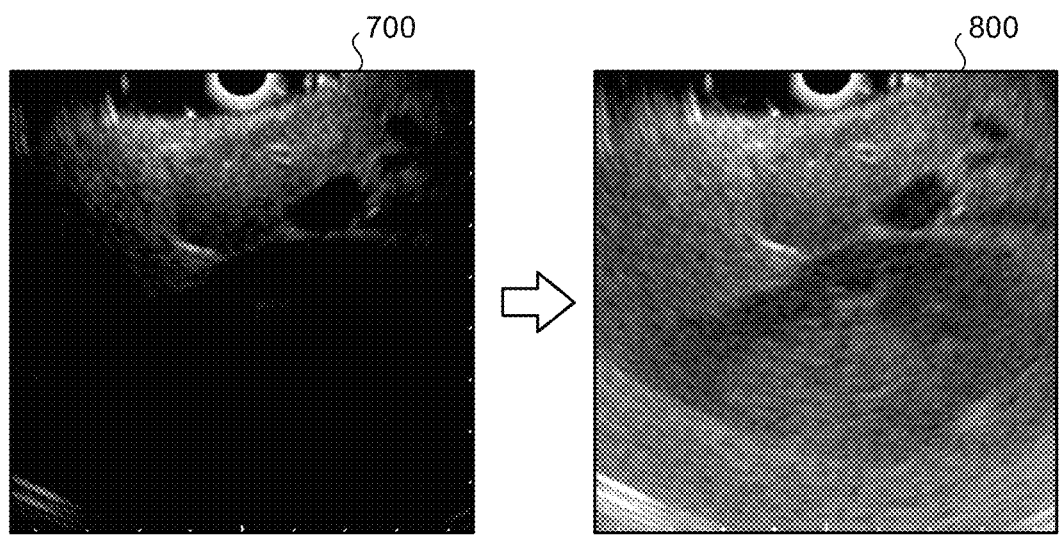
FIG. 23 is a diagram for explaining the effect of attenuation correction performed by the ultrasonic observation apparatus according to the first embodiment of the present invention.

FIG. 23 is a diagram for explaining the effect of attenuation correction performed in the first embodiment. An image 700 illustrated in FIG. 23 is a feature data image not subjected to attenuation correction. In such a case, in contrast to a B-mode image generated by the B-mode image data generating unit 51, the feature data image is a grayscale image in which the feature data b is equally assigned among R (red), G (green), and B (blue). In the feature data image 700, in the area having a large reception depth (the lower area in FIG. 23), the signal intensity decreases due to the effect of attenuation, thereby making the image darker. In contrast, regarding a feature data image 800 for which attenuation correction is performed using the same B-mode image, it can be seen that the image has got a uniform brightness throughout the screen.

According to the first embodiment of the present invention described above, in a feature data space, when a feature point of a frequency spectrum at a predetermined data position in the i-th frame (where i is a positive integer) is present within a predetermined first type area in the i-th frame and moves closer to a second type area, which has a lower priority for image display than the first type area, in the subsequent (i+1)-th frame; feature-data image data that contains information related to feature data is generated by setting a virtual feature point at a position that is far off from the second type area as compared to the position of the latest feature point and that is within or around the first type area, and by replacing visual information corresponding to the latest feature point in the (i+1)-th frame of the predetermined data position with visual information corresponding to the virtual feature point. Then, images corresponding to the feature-data image data that has been generated are displayed in a sequential manner. With that, it becomes possible to display, for as long periods of time as possible, the images having pixel values corresponding to the feature points close to the area of high priority for image display. Therefore, even if the relative position relationship with the target of observation changes with time, the desired tissues can be observed over an extended period of time.

Moreover, according to the first embodiment, the feature data is extracted by performing attenuation correction with respect to pre-correction feature data of a frequency spectrum that has been obtained by analyzing the frequencies of received ultrasonic sound waves. That extracted feature data is used along with feature data of frequency spectrums that is extracted on the basis of ultrasonic sound waves reflected from a plurality of known specimens. Hence, without having to make use of the strain amount or the degree of elasticity of the body tissues, it becomes possible to make clear distinction between different tissues. As a result, tissue characterizations can be distinguished with accuracy and the measurement result can be enhanced in terms of reliability.

Moreover, according to the first embodiment, even at the time of obtaining the feature data of known specimens, attenuation correction is performed with respect to pre-correction feature data of frequency spectrums obtained by means of frequency analysis, and the feature data obtained by performing such attenuation correction is used as the index to classify and determine tissue characterizations. Hence, it becomes possible to make distinction between mutually different tissue characterizations. Particularly, in the first embodiment, the feature data extracted by performing attenuation correction is used. Therefore, as compared to the case of using feature data that is extracted without performing attenuation correction, the area of each group in the feature data space can be obtained in a more distinctly separated state.

During ultrasonic elastography, the pressure applied by pressing does not easily reach the inferior regions of vascular channels such as blood vessels or lymph vessels. For that reason, if a tumor is formed in the vicinity of a vascular channel, the boundary of the tumor remains ambiguous and it is difficult to identify the invasion of the tumor into the vascular channel. Hence, there are times when the specimen cannot be observed with accuracy. Moreover, during ultrasonic elastography, the amount of pressure or the pressing speed that gets applied while pressing the body part to be examined can easily differ from person to person who is conducting the examination. That leads to a low degree of reliability in the observation result. In that regard, according to the first embodiment, as described above, since a specimen is observed with a high degree of accuracy, it is possible to achieve enhancement in terms of reliability. As a result, it becomes possible to provide a technology that is suitable in resolving the issues specific to ultrasonic elastography.

Second Embodiment

In a second embodiment of the present invention, the feature-data image data generating operation performed by a feature-data image data generating unit is different than the first embodiment. The configuration of an ultrasonic observation apparatus according to the second embodiment is same as the configuration of the ultrasonic observation apparatus 1 according to the first embodiment. Thus, in the following explanation, the constituent elements identical to those in the ultrasonic observation apparatus 1 are referred to by the same reference numerals.

In the second embodiment, the feature data information storing unit 85 also stores therein a boundary feature point $U_i(j)$, which is either the feature point $S_i(j)$ or the residual image feature point $T_i(j)$ used in calculating the pixel value and which is used in the subsequent frame for the purpose of setting a boundary that is required at the time of determining the residual image condition in the feature data space.

Figure 24:
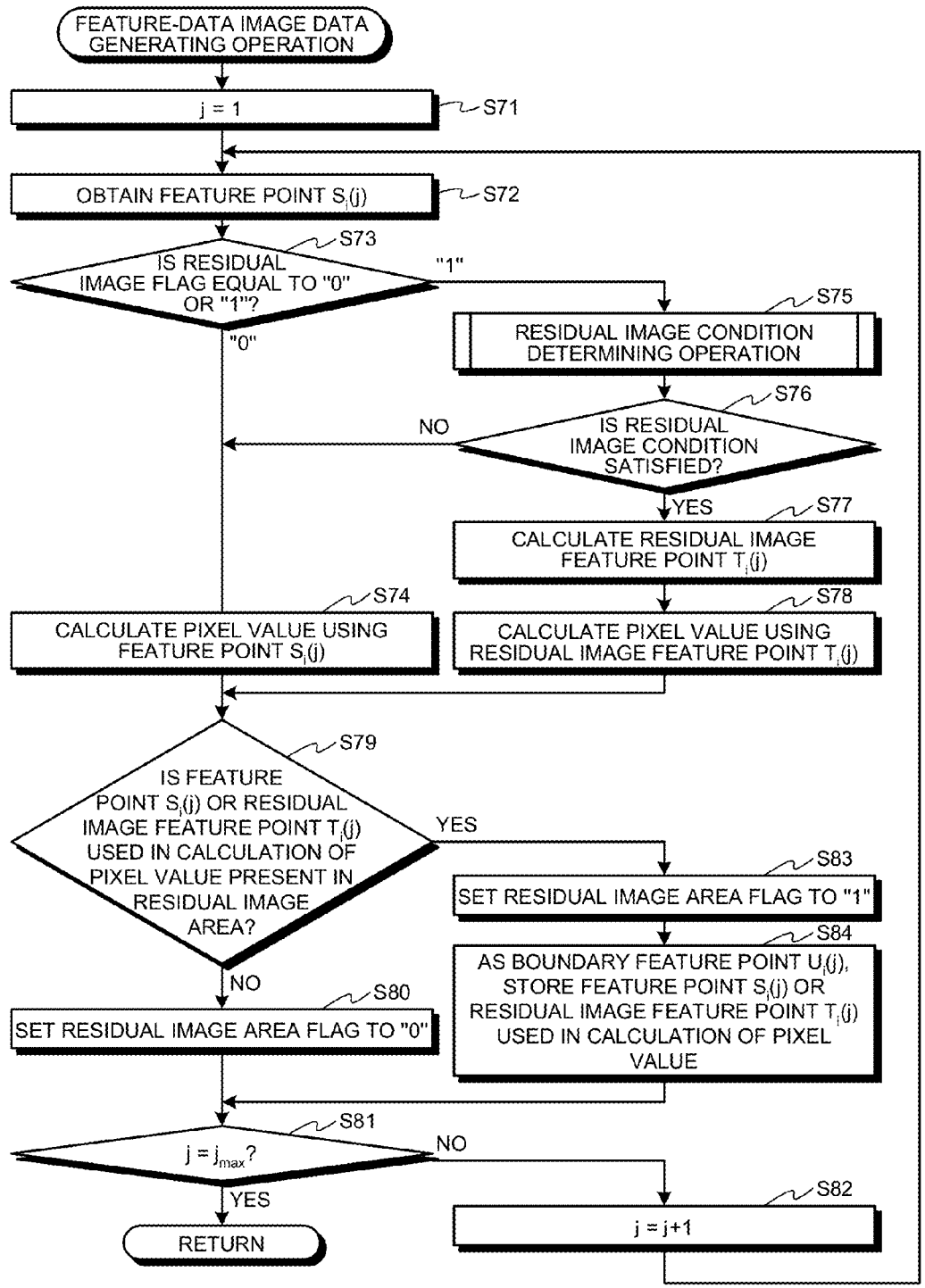
FIG. 24 is a flowchart for explaining an overview of a feature-data image data generating operation performed by the feature-data image data generating unit of the ultrasonic observation apparatus according to a second embodiment of the present invention.

FIG. 24 is a flowchart for explaining an overview of a feature-data image data generating operation performed by the feature-data image data generating unit 52 of the ultrasonic observation apparatus 1 according to the second embodiment. With reference to FIG. 24, the feature-data image data generating unit 52 sets the variable j for pixel identification to "1" (Step S71).

Then, the feature-data image data generating unit 52 obtains the feature point (third feature point) $S_i(j)$ that has been extracted by the feature data extracting unit 42 (Step S72), reads the residual image area flag of that feature point $S_i(j)$ from the feature-data-space information storing unit 84, and determines the value of the residual image area flag (Step S73). If the residual image area flag is "0" (0 at Step S73), then the feature-data image data generating unit 52 calculates the pixel value of the pixel j using the feature point $S_i(j)$ (Step S74).

On the other hand, if the residual image area flag of the feature point $S_i(j)$ is "1" (1 at Step S73), then the feature-data image data generating unit 52 determines whether or not a residual image condition is satisfied (Step S75).

Figure 25:
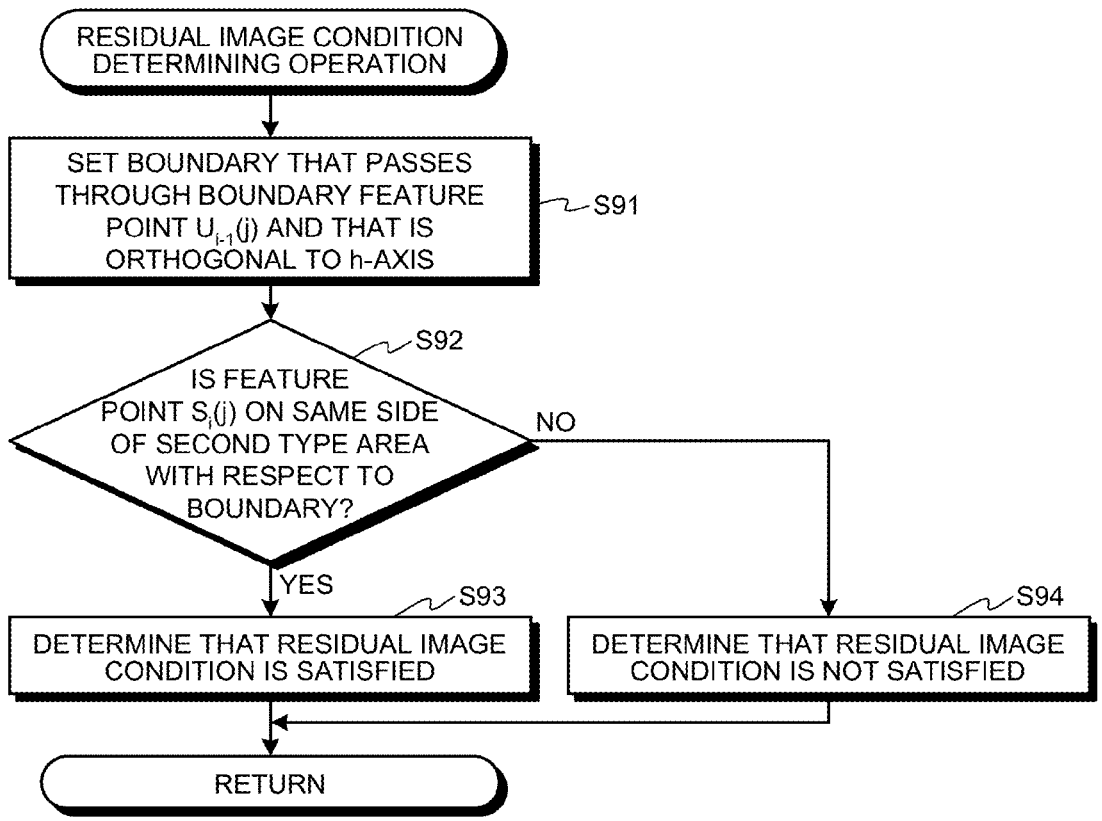
FIG. 25 is a flowchart for explaining an overview of a residual image condition determining operation performed by the feature-data image data generating unit of the ultrasonic observation apparatus according to the second embodiment of the present invention.

FIG. 25 is a flowchart for explaining an overview of a residual image condition determining operation. With reference to FIG. 25, firstly, the feature-data image data generating unit 52 sets a reference boundary that passes through a boundary feature point $U_{i-1}(j)$ in the feature data space and that is orthogonal to the reference axis (h-axis) (Step S91).

Figure 26:
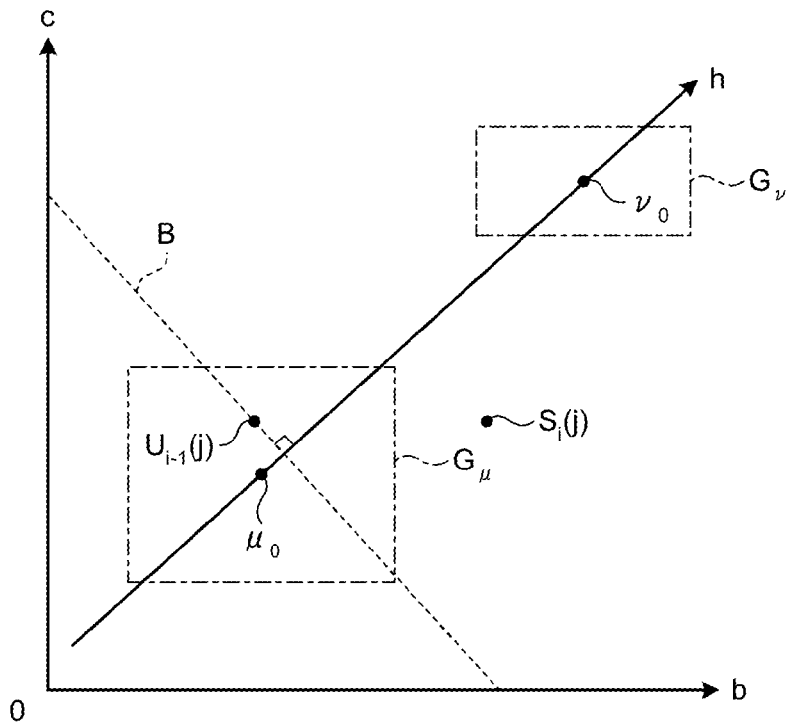
FIG. 26 is a diagram illustrating a configuration of a feature data space in a case during the residual image condition determining operation, which is performed by the feature-data image data generating unit of the ultrasonic observation apparatus according to the second embodiment of the present invention, when it is determined that a residual image condition is satisfied.

Then, the feature-data image data generating unit 52 determines whether or not the feature point $S_i(j)$ is positioned on the same side of the second type area with respect to the reference boundary (Step S92). If the feature point $S_i(j)$ is positioned on the same side of the second type area with respect to the reference boundary (Yes at Step S92), then the feature-data image data generating unit 52 determines that the residual image condition is satisfied (Step S93), and the system control proceeds to Step S76. FIG. 26 is a diagram illustrating a configuration of the feature data space when the residual image condition is determined to be satisfied during the residual image condition determining operation performed in the ultrasonic observation apparatus 1. With reference to FIG. 26, with respect to a reference boundary B that is a straight line passing through the boundary feature point $U_{i-1}(j)$ and orthogonal to the h-axis, the feature point $S_i(j)$ is positioned on the same side of the area $G_v$ serving as the second type area. Meanwhile, when the feature data space is a three-dimensional space, the reference boundary is a plane.

Figure 27:
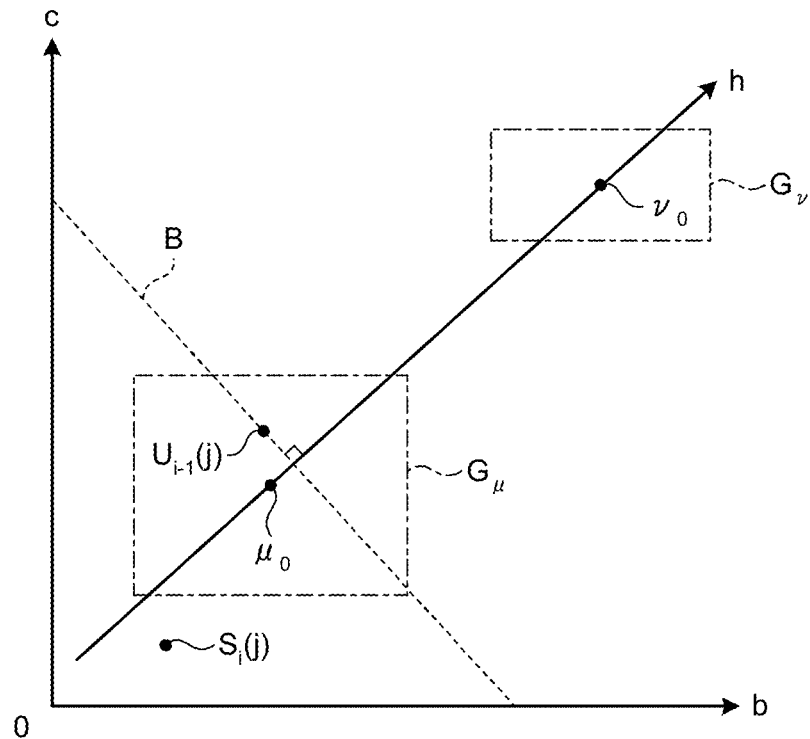
FIG. 27 is a diagram illustrating a configuration of a feature data space in a case during the residual image condition determining operation, which is performed by the feature-data image data generating unit of the ultrasonic observation apparatus according to the second embodiment of the present invention, when it is determined that the residual image condition is not satisfied.

On the other hand, if the feature point $S_i(j)$ is not positioned on the same side of the second type area with respect to the reference boundary (No at Step S92), then the feature-data image data generating unit 52 determines that the residual image condition is not satisfied (Step S94), and the system control proceeds to Step S76. FIG. 27 is a diagram illustrating a configuration of the feature data space when the residual image condition is determined to be not satisfied during the residual image condition determining operation performed in the ultrasonic observation apparatus 1. With reference to FIG. 27, with respect to the reference boundary B, the feature point $S_i(j)$ is positioned on the other side of the area $G_v$.

Returning to the explanation with reference to FIG. 24, if the result of the residual image condition determining operation at Step S75 indicates that the residual image condition is satisfied (Yes at Step S76), then the feature-data image data generating unit 52 calculates the residual image feature point $T_i(j)$ (fourth feature point) (Step S77).

Figure 28:
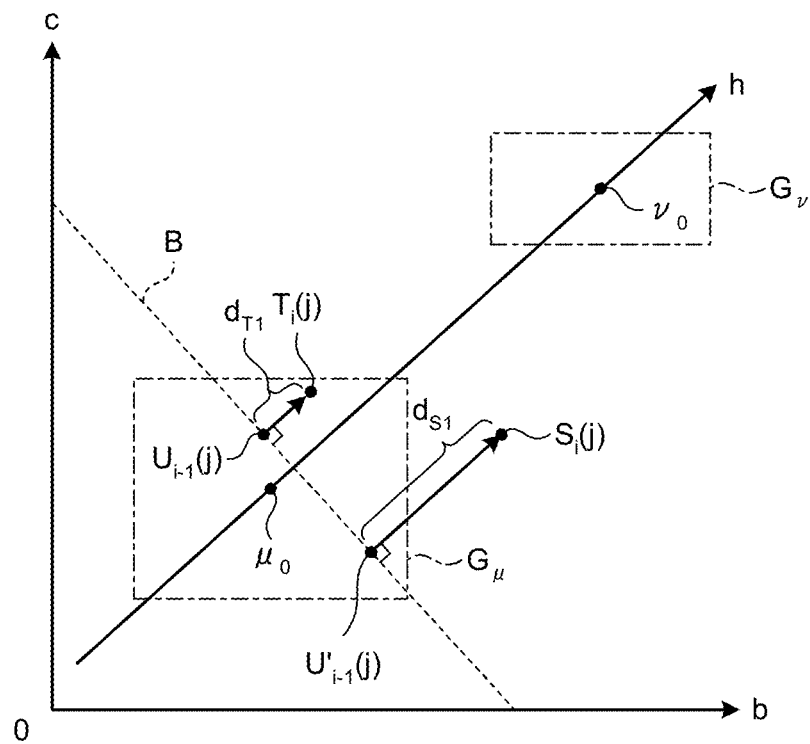
FIG. 28 is a diagram illustrating an overview (first example) of a residual image feature point calculating operation performed by the ultrasonic observation apparatus according to the second embodiment of the present invention.

FIG. 28 is a diagram illustrating an overview (first example) of the residual image feature point calculating operation performed at Step S77. Firstly, the feature-data image data generating unit 52 obtains an intersection point $U'_{i-1}(j)$ of a straight line passing through the feature point $S_i(j)$ and orthogonal to the reference boundary B (i.e., a straight line that is parallel to the h-axis) with the reference boundary B, and calculates a distance $d_{S1}$ between the intersection point $U'_{i-1}(j)$ and the feature point $S_i(j)$. Then, the feature-data image data generating unit 52 sets the residual image feature point $T_i(j)$ to a point that is spaced apart from the boundary feature point $U_{i-1}(j)$ by a distance $d_{T1}=d_{S1}/n$ (where n>1, n is a constant number), that is closer to the area $G_v$ as compared to the boundary feature point $U_{i-1}(j)$, and that lies on a straight line which passes through the boundary feature point $U_{i-1}(j)$ and which is orthogonal to the reference boundary B. Meanwhile, the distance $d_{T1}$ can also be defined as a constant value.

Subsequently, the feature-data image data generating unit 52 calculates the pixel value of the pixel j using the residual image feature point $T_i(j)$ (Step S78).

Meanwhile, at Step S76, if the residual condition is not satisfied (No at Step S76); then the system control proceeds to Step S74.

After the operation at Step S74 or Step S78 is completed, the feature-data image data generating unit 52 determines whether the feature point $S_i(j)$ or the residual image feature point $T_i(j)$ used in calculating the pixel value is present in the residual image area (Step S79). When the feature point $S_i(j)$ or the residual image feature point $T_i(j)$ is not present in the residual image area (No at Step S79), then the feature-data image data generating unit 52 sets the residual image area flag to "0" (Step S80).

Then, if the variable j for identifying pixel values has reached the maximum value $j_{max}$ (Yes at Step S81), the feature-data image data generating unit 52 ends the feature-data image data generating operation. In contrast, if the variable j for identifying pixel values is smaller than the maximum value $j_{max}$ (No at Step S81), the feature-data image data generating unit 52 increments the variable j by 1 (Step S82), and the system control returns to Step S72. Herein too, the increment in the variable j means nothing more than a change in the pixel to be processed. Thus, there is no change in variables such as the feature point and the residual image feature point that are assigned to the pixels on an individual basis.

The following explanation is given for the case when, at Step S79, the feature point $S_i(j)$ or the residual image feature point $T_i(j)$ is present in the residual image area (Yes at Step S79). In this case, the feature-data image data generating unit 52 sets the residual image area flag to "1" (Step S83); and stores the feature point $S_i(j)$ or the residual image feature point $T_i(j)$, which is used in calculating the pixel value, as the boundary feature point $U_i(j)$ in the feature data information storing unit 85 (Step S84). Then, the system control proceeds to Step S81.

According to the second embodiment of the present invention described above, in a feature data space, when a feature point of a frequency spectrum at a predetermined data position is present within a predetermined first type area in the i-th frame (where i is a positive integer) and moves closer to a second type area, which has a lower priority for image display than the first type area, in the subsequent (i+1)-th frame; feature-data image data that contains information related to feature data is generated by setting a virtual feature point at a position that is far off from the second type area as compared to the position of the latest feature point and that is within or around the first type area, and by replacing visual information corresponding to the latest feature point in the (i+1)-th frame of the predetermined data position with visual information corresponding to the virtual feature point. Then, images corresponding to the feature-data image data that has been generated are displayed in a sequential manner. With that, it becomes possible to display, for as long periods of time as possible, the images having pixel values corresponding to the feature points close to the area of high priority for image display. Therefore, even if the relative position relationship with the target of observation changes with time, the desired tissues can be observed over an extended period of time.

Moreover, according to the second embodiment, the feature data is extracted by performing attenuation correction with respect to pre-correction feature data of a frequency spectrum that has been obtained by analyzing the frequencies of received ultrasonic sound waves. That extracted feature data is used along with feature data of frequency spectrums that is extracted on the basis of ultrasonic sound waves reflected from a plurality of known specimens. Hence, without having to make use of the strain amount or the degree of elasticity of the body tissues, it becomes possible to make clear distinction between different tissues. As a result, tissue characterizations can be distinguished with accuracy and the measurement result can be enhanced in terms of reliability. Hence, it becomes possible to provide a technology that is suitable to ultrasonic elastography.

Figure 29:
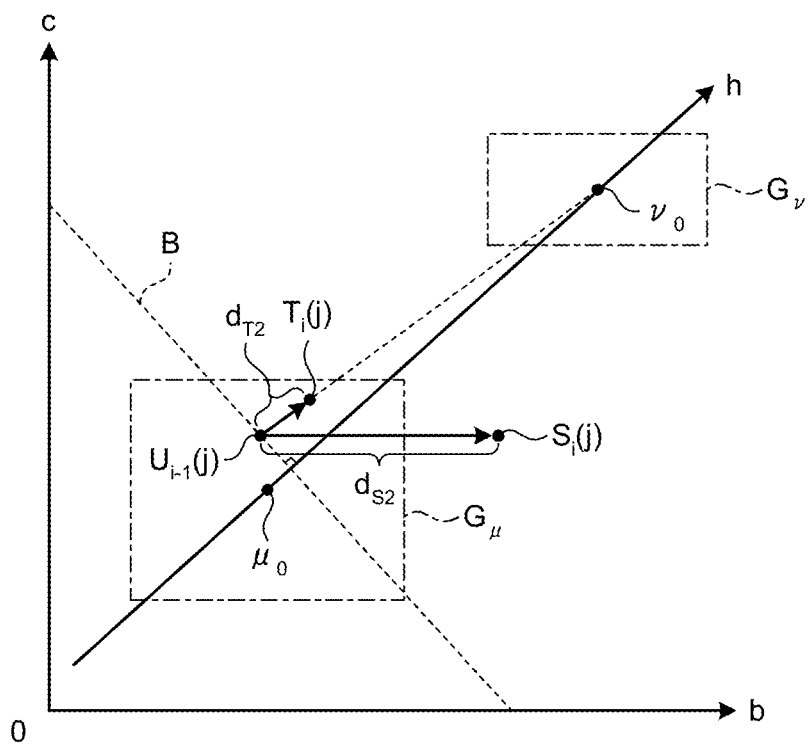
FIG. 29 is a diagram illustrating an overview (second example) of the residual image feature point calculating operation performed by the ultrasonic observation apparatus according to the second embodiment of the present invention.

FIG. 29 is a diagram illustrating another example (second example) of an overview of the residual image feature point calculating operation performed at Step S77 illustrated in FIG. 24. Firstly, the feature-data image data generating unit 52 calculates a distance $d_{S2}$ between the boundary feature point $U_{i-1}(j)$ and the feature point $S_i(j)$. Then, the feature-data image data generating unit 52 sets the residual image feature point $T_i(j)$ to a point that is spaced apart from the boundary feature point $U_{i-1}(j)$ by a distance $d_{T2}=d_{S2}/n$ (where n>1, n is a constant number), that is closer to the area $G_v$ as compared to the boundary feature point $U_{i-1}(j)$, and that lies on a straight line which passes through the boundary feature point $U_{i-1}(j)$ and through the representative point $v_0$.

Third Embodiment

In a third embodiment of the present invention, the feature data extracting operation performed by a feature data extracting unit is different than the first embodiment. The configuration of an ultrasonic observation apparatus according to the third embodiment is same as the configuration of the ultrasonic observation apparatus 1 according to the first embodiment. Thus, in the following explanation, the constituent elements identical to those in the ultrasonic observation apparatus 1 are referred to by the same reference numerals.

During the feature data extracting operation according to the third embodiment, firstly, the attenuation correcting unit 422 performs attenuation correction with respect to the frequency spectrum calculated by the frequency analyzing unit 41. Then, the approximating unit 421 performs approximation with respect to the frequency spectrum that has been subjected to attenuation correction by the attenuation correcting unit 422, and extracts the feature data of the frequency spectrum.

Figure 30:
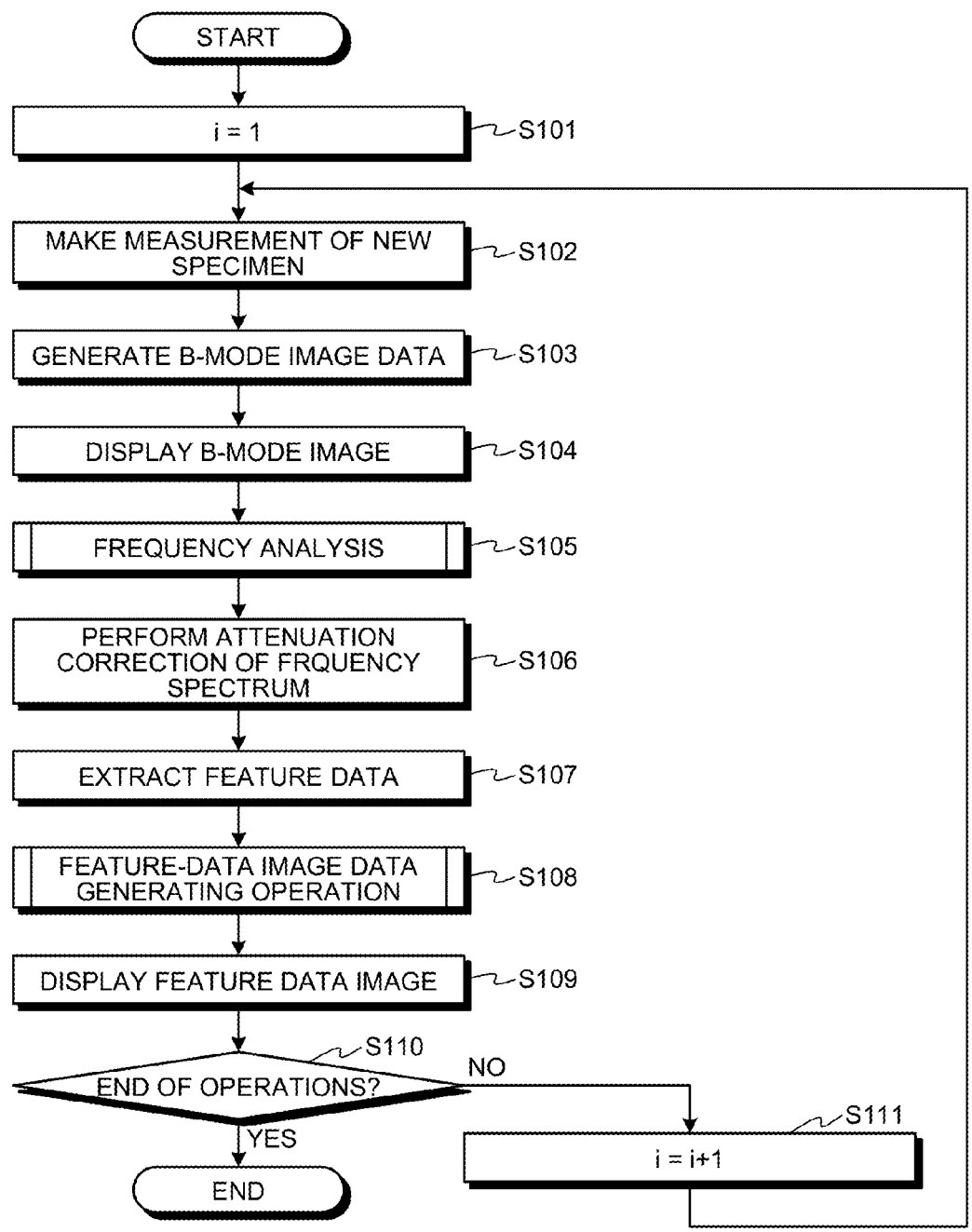
FIG. 30 is a flowchart for explaining an overview of the operations performed by the ultrasonic observation apparatus according to a third embodiment of the present invention.

FIG. 30 is a flowchart for explaining an overview of the operations performed by the ultrasonic observation apparatus according to the third embodiment. With reference to FIG. 30, the operations performed at Step S101 to Step S105 are respectively identical to the operations performed at Step S1 to Step S5 illustrated in FIG. 3.

Figure 31:
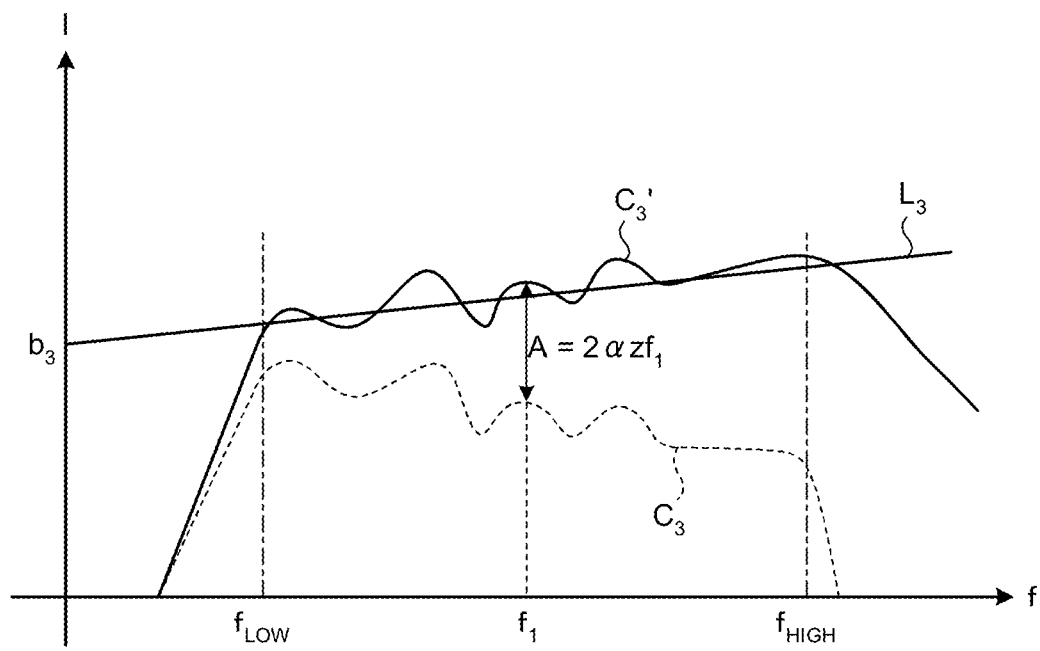
FIG. 31 is a diagram that schematically illustrates an overview of attenuation correction performed by the ultrasonic observation apparatus according to the third embodiment of the present invention.

At Step S106, the attenuation correcting unit 422 performs attenuation correction with respect to all frequency spectrums that are calculated by the frequency analyzing unit 41 by means of FFT (Step S106). FIG. 31 is a diagram that schematically illustrates an overview of the operation performed at Step S106. As illustrated in FIG. 31, with respect to a frequency spectrum curve $C_3$, the attenuation correcting unit 422 performs correction in the form of adding the attenuation amount A given in Equation (1) to the intensity I for all frequencies f, and obtains a new frequency spectrum curve $C_3'$. As a result, it becomes possible to obtain a frequency spectrum in which the contribution of attenuation occurring due to the propagation of ultrasonic sound waves is reduced.

Subsequently, the approximating unit 421 performs regression analysis of all frequency spectrums that are subjected to attenuation correction by the attenuation correcting unit 422, and extracts the feature data of the frequency spectrums (Step S107). More particularly, the approximating unit 421 performs regression analysis and calculates the gradient a, the intercept b, and the intensity c at the central frequency $f_{MID}$, which characterize the linear expression. A straight line $L_3$ illustrated in FIG. 31 is a regression line (intercept $b_3$) obtained by performing the feature data extracting operation on the frequency spectrum curve $C_3$ at Step S107.

The operations performed at Step S108 to Step S111 are respectively identical to the operations performed at Step S8 to Step S11 illustrated in FIG. 3.

According to the third embodiment of the present invention described above, in a feature data space, when a feature point of a frequency spectrum at a predetermined data position is present within a predetermined first type area in the i-th frame (where i is a positive integer) and moves closer to a second type area, which has a lower priority for image display than the first type area, in the subsequent (i+1)-th frame; feature-data image data that contains information related to feature data is generated by setting a virtual feature point at a position that is far off from the second type area as compared to the position of the latest feature point and that is within or around the first type area, and by replacing visual information corresponding to the latest feature point in the (i+1)-th frame of the predetermined data position with visual information corresponding to the virtual feature point. Then, images corresponding to the feature-data image data that has been generated are displayed in a sequential manner. With that, it becomes possible to display, for as long periods of time as possible, the images having pixel values corresponding to the feature points close to the area of high priority for image display. Therefore, even if the relative position relationship with the target of observation changes with time, the desired tissues can be observed over an extended period of time.

Moreover, according to the third embodiment, attenuation correction is performed with respect to a frequency spectrum that has been obtained by analyzing the frequencies of received ultrasonic sound waves, and feature data is extracted from the frequency spectrum that has been subjected to attenuation correction. That extracted feature data is used along with feature data of frequency spectrums that is extracted on the basis of ultrasonic sound waves reflected from a plurality of known specimens. Hence, without having to make use of the strain amount or the degree of elasticity of the body tissues, it becomes possible to make clear distinction between different tissues. As a result, tissue characterizations can be distinguished with accuracy and the measurement result can be enhanced in terms of reliability. Hence, it becomes possible to provide a technology that is suitable to ultrasonic elastography.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic observation apparatus that transmits ultrasonic sound waves to a specimen and receives ultrasonic sound waves reflected from the specimen, the ultrasonic observation apparatus comprising:
   a frequency analyzing unit that calculates frequency spectrums at a plurality of data positions which are set with respect to the ultrasonic sound waves that have been received;
   a feature data extracting unit that performs approximation with respect to the frequency spectrums calculated by the frequency analyzing unit and extracts a single set or a plurality of sets of feature data of the frequency spectrums;
   an image processing unit that sequentially generates feature-data image data containing information related to the feature data extracted by the feature data extracting unit; and
   a display unit that sequentially displays images corresponding to the feature-data image data generated sequentially by the image processing unit, wherein
   in a feature data space in which it is possible to set a coordinate system having at least some of the single set or the plurality of sets of feature data as coordinate components, when a feature point of a frequency spectrum at a particular data position is present within a predetermined first type area in an i-th frame (where i is a positive integer) in the display unit and moves closer to a second type area, which has a lower priority for image display than the first type area, in subsequent (i+1)-th frame,
   the image processing unit generates the feature-data image data by setting a virtual feature point at a position that is far off from the second type area as compared to the position of latest feature point and that is within or around the first type area, and by replacing visual information corresponding to the latest feature point in the (i+1)-th frame of the predetermined data position with visual information corresponding to the virtual feature point.

2. The ultrasonic observation apparatus according to claim 1, wherein the image processing unit projects a first feature point and a second feature point, which are feature points of a frequency spectrum at same data position and which are calculated at the time of respectively generating the (i+1)-th frame and generating the i-th frame, on a reference axis passing through a representative point of the first type area and a representative point of the second type area, and determines positional relationship of the first representative point and the second representative point with the second type area based on distances from projected points to the representative point of the second type area.

3. The ultrasonic observation apparatus according to claim 2, wherein
   the first representative point is a feature point determined from the feature data extracted by the feature data extracting unit, and
   the second representative point is the virtual feature point.

4. The ultrasonic observation apparatus according to claim 1, wherein
   the image processing unit determines positional relationship of the feature point that is used in generating the (i+1)-th frame with the second type area while considering, as a reference boundary, a straight line or a plane that is orthogonal to the reference axis passing through representative points of the first type area and the second type area and that passes through either one of a third feature point and a fourth feature point calculated as feature points at same data position,
   the third representative point is a feature point determined from the feature data extracted by the feature data extracting unit, and
   the fourth representative point is the virtual feature point.

5. The ultrasonic observation apparatus according to claim 4, wherein the image processing unit determines the position of the virtual feature point in the (i+1)-th frame by referring to the position of the feature point included in the reference boundary from among the third feature point and the fourth feature point in the i-th frame and by referring to the reference axis.

6. The ultrasonic observation apparatus according to claim 4, wherein the image processing unit determines the position of the virtual feature point in the (i+1)-th frame by referring to the position of the feature point included in the reference boundary from among the third feature point and the fourth feature point in the i-th frame and by referring to the position of the representative point of the second type area.

7. The ultrasonic observation apparatus according to claim 1, wherein the feature data extracting unit extracts the feature data by performing attenuation correction, by which there is a decrease in the contribution of attenuation that occurs due to the reception depth and the frequency of ultrasonic sound waves being propagated, and approximation with respect to the frequency spectrums calculated by the frequency analyzing unit.

8. The ultrasonic observation apparatus according to claim 7, wherein the feature data extracting unit includes
an approximating unit that performs the approximation with respect to the frequency spectrums calculated by the frequency analyzing unit and extracts pre-correction feature data as feature data prior to performing the attenuation correction; and
an attenuation correcting unit that performs the attenuation correction with respect to the pre-correction feature data extracted by the approximating unit, and extracts feature data of the frequency spectrums.

9. The ultrasonic observation apparatus according to claim 8, wherein, greater the reception depth of ultrasonic sound waves, greater is the extent of correction performed by the attenuation correcting unit.

10. The ultrasonic observation apparatus according to claim 8, wherein the approximating unit performs polynomial approximation with respect to the frequency spectrums by means of regression analysis.

11. The ultrasonic observation apparatus according to claim 7, wherein the feature data extracting unit includes
an attenuation correcting unit that performs the attenuation correction with respect to the frequency spectrums; and
an approximating unit that performs the approximation with respect to the frequency spectrums corrected by the attenuation correcting unit, and extracts feature data of the frequency spectrums.

12. The ultrasonic observation apparatus according to claim 11, wherein the approximating unit performs polynomial approximation with respect to the frequency spectrums by means of regression analysis.

13. The ultrasonic observation apparatus according to claim 1, wherein the visual information points to variables constituting a color space.

14. An operation method of an ultrasonic observation apparatus that transmits ultrasonic sound waves to a specimen and receives ultrasonic sound waves reflected from the specimen, the operation method comprising:
calculating, by a frequency analyzing unit, that includes analyzing frequencies of the received ultrasonic sound waves and calculating a frequency spectrum;
extracting that includes performing approximation with respect to the frequency spectrum and extracting a single set or a plurality of sets of feature data of the frequency spectrum;
generating, by an image processing unit, that includes generating feature-data image data containing information related to the feature data; and
displaying, by a displaying unit, that includes displaying an image corresponding to the feature-data image data, wherein
the calculating that includes calculating the frequency spectrum up to the displaying that includes displaying the image is performed in a repeated manner, and
in a feature data space in which it is possible to set a coordinate system having at least some of the single set or the plurality of sets of feature data as coordinate components, when a feature point of a frequency spectrum at a particular data position is present within a predetermined first type area in an i-th frame (where i is a positive integer) in the display unit and moves closer to a second type area, which has a lower priority for image display than the first type area, in subsequent (i+1)-th frame, the feature-data image data is generated by setting a virtual feature point at a position that is far off from the second type area as compared to the position of latest feature point and that is within or around the first type area, and by replacing visual information corresponding to the latest feature point in the (i+1)-th frame of the predetermined data position with visual information corresponding to the virtual feature point.

15. A non-transitory computer readable recording medium with an executable program stored thereon, wherein the program instructs a processor to perform:
calculating, by a frequency analyzing unit, that includes analyzing frequencies of the received ultrasonic sound waves and calculating a frequency spectrum;
extracting that includes performing approximation with respect to the frequency spectrum and extracting a single set or a plurality of sets of feature data of the frequency spectrum;
generating, by an image processing unit, that includes generating feature-data image data containing information related to the feature data; and
displaying, by a displaying unit, that includes displaying an image corresponding to the feature-data image data, wherein
the calculating that includes calculating the frequency spectrum up to the displaying that includes displaying the image is performed in a repeated manner, and
in a feature data space in which it is possible to set a coordinate system having at least some of the single set or the plurality of sets of feature data as coordinate components, when a feature point of a frequency spectrum at a particular data position is present within a predetermined first type area in an i-th frame (where i is a positive integer) in the display unit and moves closer to a second type area, which has a lower priority for image display than the first type area, in subsequent (i+1)-th frame, the feature-data image data is generated by setting a virtual feature point at a position that is far off from the second type area as compared to the position of latest feature point and that is within or around the first type area, and by replacing visual information corresponding to the latest feature point in the (i+1)-th frame of the predetermined data position with visual information corresponding to the virtual feature point.

* * * * *